(12) United States Patent
Farr et al.

(10) Patent No.: US 8,328,815 B2
(45) Date of Patent: Dec. 11, 2012

(54) SURGICAL ACCESS WITH TARGET VISUALIZATION

(75) Inventors: Morteza M. Farr, Santa Cruz, CA (US);
E. Marlowe Goble, Logan, UT (US); T. Wade Fallin, Hyde Park, UT (US);
Ephraim Akyuz, Providence, UT (US);
Daniel F. Justin, Logan, UT (US);
Douglas M. Lorang, North Logan, UT (US)

(73) Assignee: Innovative Spine, LLC., Clovis, CA (US)

( * ) Notice: Subject to any disclaimer, the term of this patent is extended or adjusted under 35 U.S.C. 154(b) by 608 days.

(21) Appl. No.: 12/537,941

(22) Filed: Aug. 7, 2009

(65) Prior Publication Data
US 2010/0030065 A1    Feb. 4, 2010

Related U.S. Application Data

(63) Continuation-in-part of application No. 12/357,596, filed on Jan. 22, 2009, and a continuation-in-part of application No. 11/934,636, filed on Nov. 2, 2007, and a continuation-in-part of application No. 11/831,698, filed on Jul. 31, 2007, now Pat. No. 8,025,664, application No. 12/537,941, which is a continuation-in-part of application No. 11/831,728, filed on Jul. 31, 2007, now Pat. No. 8,057,481.

(60) Provisional application No. 60/856,682, filed on Nov. 3, 2006, provisional application No. 61/086,940, filed on Aug. 7, 2008, provisional application No. 61/023,030, filed on Jan. 23, 2008, provisional application No. 61/050,523, filed on May 5, 2008.

(51) Int. Cl.
*A61B 17/58* (2006.01)

(52) U.S. Cl. ..................................... 606/99; 606/86 A
(58) Field of Classification Search ............. 606/90, 606/96, 99, 86 A, 279
See application file for complete search history.

(56) References Cited

U.S. PATENT DOCUMENTS 5,203,777 A    4/1993  Lee
5,921,978 A *  7/1999  Thompson et al. ........... 604/529

(Continued)

OTHER PUBLICATIONS

International Search Report and Written Opinion From Corresponding PCT Application No. PCT/US2009/053217, Mar. 15, 2010 (13 pgs).

*Primary Examiner* — Thomas Barrett
*Assistant Examiner* — Melissa A Golob
(74) *Attorney, Agent, or Firm* — GSS Law Group

(57) ABSTRACT

Accessing a spine from a curved postero-lateral approach may include a curved cannula positioned along a curved path from an opening in the skin to a location proximate to the spine. Positioning of the distal end of a radiolucent curved access cannula may be assisted by use of one or more radio-opaque markers. Markers may be positioned to form a cross hair image in fluoroscopy to assist in cannula placement. Radio-opaque inserts placed in and extended beyond the curved access cannula may have radiolucent windows to allow viewing of the cannula's radio-opaque markers. An appropriately placed curved access cannula may be clamped to prevent subsequent movement. Appropriate tools may be introduced through the curved access cannula and the distal radio-opaque tool heads may be viewed relative to the radio-opaque markers. The curved access cannula may be attached to the spine through one or more screws.

14 Claims, 38 Drawing Sheets

U.S. PATENT DOCUMENTS

| | | | | |
|---|---|---|---|---|
| 2002/0138079 A1* | 9/2002 | Cohen | | 606/99 |
| 2003/0050644 A1* | 3/2003 | Boucher et al. | | 606/90 |
| 2003/0065329 A1* | 4/2003 | Vaughan | | 606/61 |
| 2003/0229347 A1 | 12/2003 | Sherman et al. | | |
| 2006/0149278 A1* | 7/2006 | Abdou | | 606/90 |
| 2007/0010844 A1 | 1/2007 | Gong et al. | | |

* cited by examiner

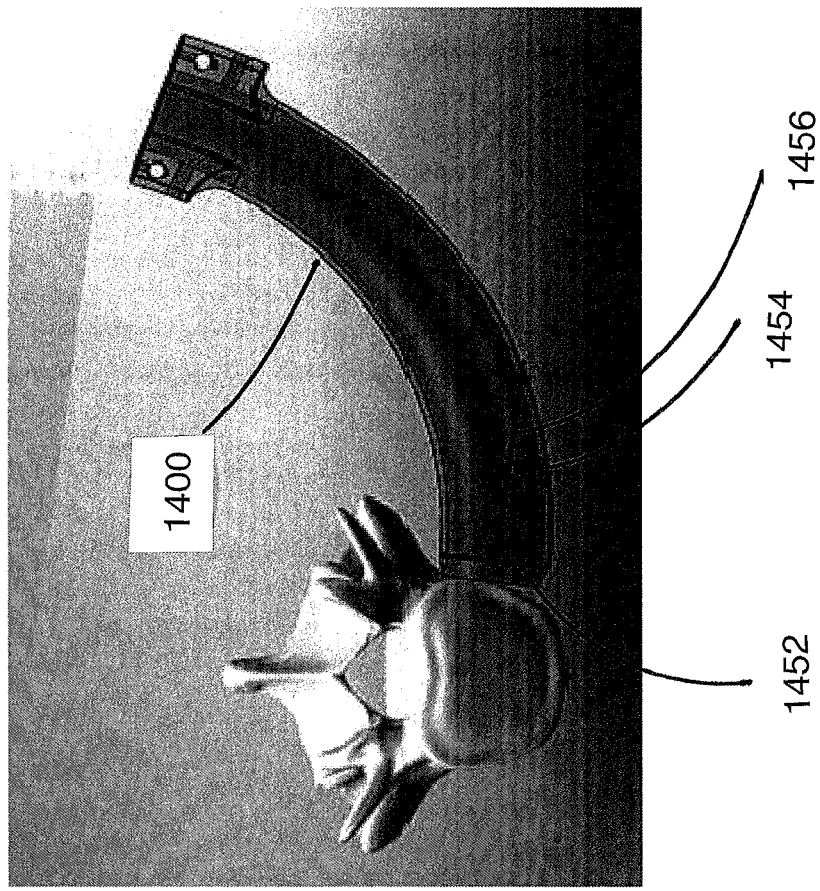
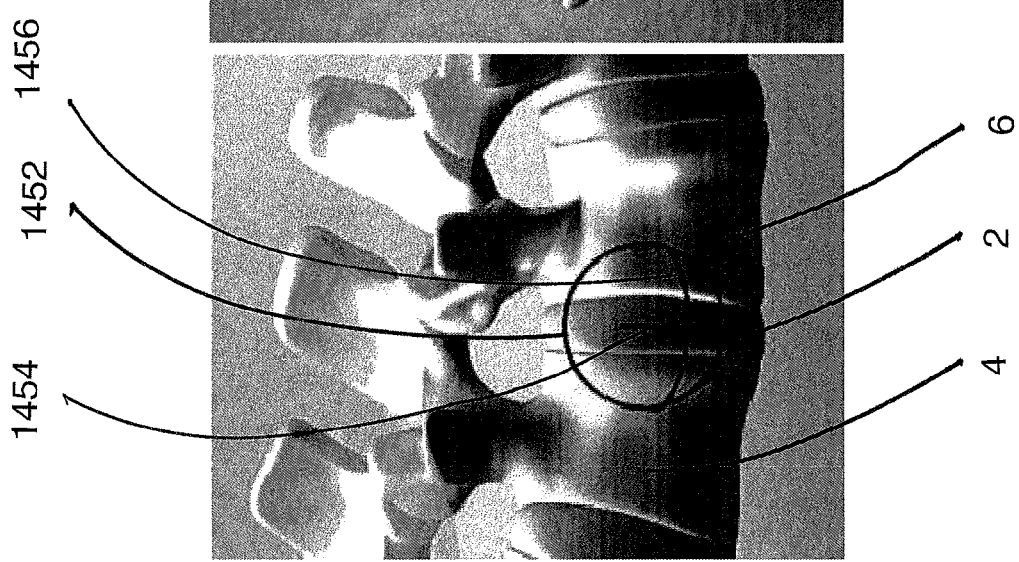
FIG. 28A
FIG. 28B

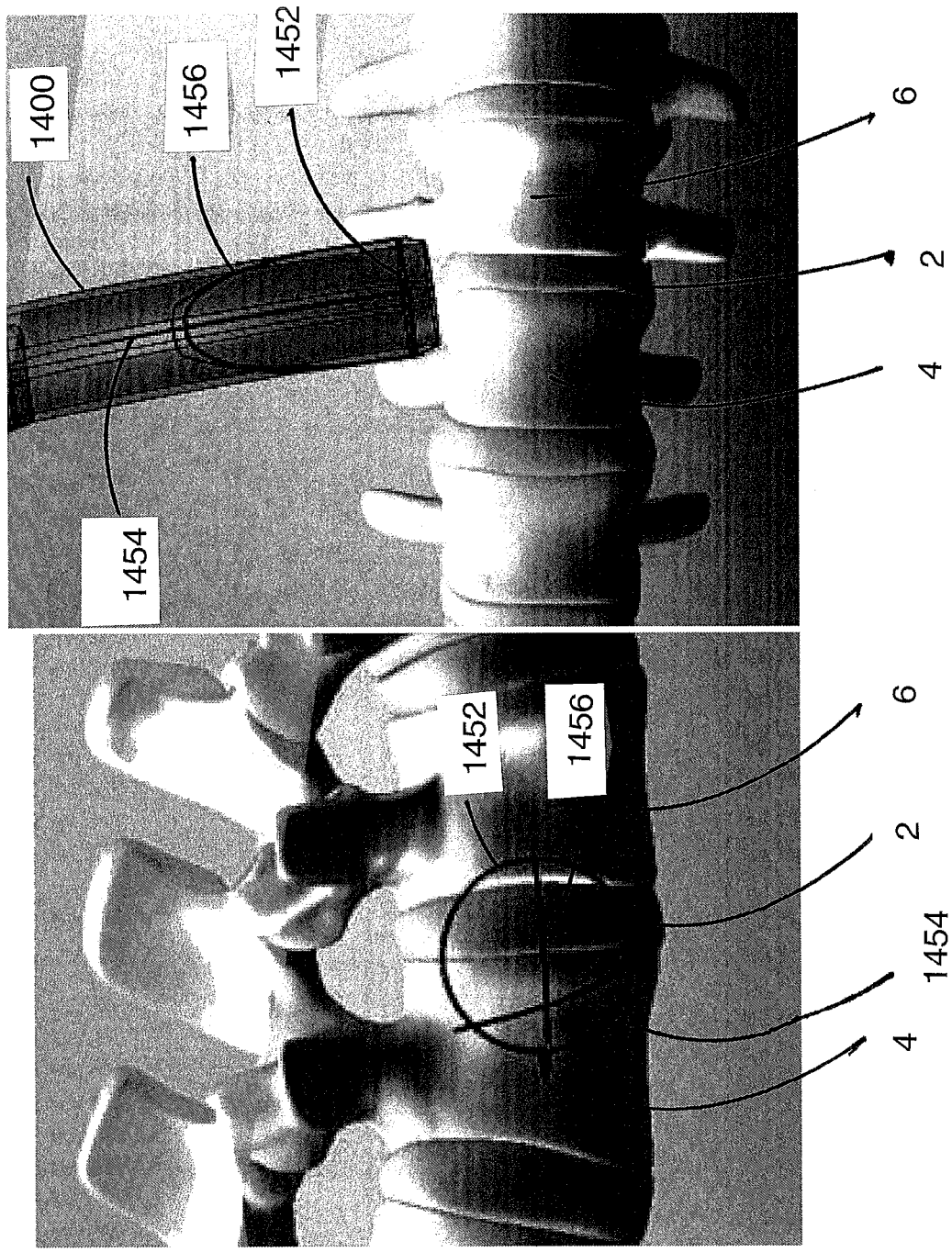

SURGICAL ACCESS WITH TARGET VISUALIZATION

CROSS-REFERENCE TO RELATED APPLICATIONS

This application is a continuation-in-part of:

Pending prior U.S. patent application Ser. No. 11/831,698, filed Jul. 31, 2007, and with title SYSTEM AND METHOD FOR PROVIDING SURGICAL ACCESS TO A SPINE;

Pending prior U.S. patent application Ser. No. 11/831,728, filed Jul. 31, 2007, with title SYSTEM AND METHOD FOR PROVIDING SURGICAL ACCESS TO A SPINE; and Pending prior U.S. patent application Ser. No. 11/934,636, filed Nov. 2, 2007, with title INSTRUMENTATION AND METHOD FOR PROVIDING SURGICAL ACCESS TO A SPINE, each of which claims the benefit of:

U.S. Provisional Patent Application No. 60/856,682, filed Nov. 3, 2006, which has title METHOD AND APPARATUS FOR SPINAL SURGERY.

This application also claims the benefit of the following:

Pending prior U.S. Provisional Patent Application No. 61/086,940, filed Aug. 7, 2008, titled SYSTEMS AND METHODS FOR SURGICAL ACCESS AND VISUALIZATION;

Pending prior U.S. patent application Ser. No. 12/357,596, filed Jan. 22, 2009, titled SPINAL ACCESS SYSTEM AND METHODS, which in turn claims priority to:

Pending prior U.S. Provisional Patent Application No. 61/023,030, filed Jan. 23, 2008, titled SYSTEMS AND METHODS FOR SURGICAL ACCESS AND VISUALIZATION; and Pending prior U.S. Provisional Patent Application No. 61/050,523, filed May 5, 2008, titled SPINAL ACCESS SYSTEMS AND METHODS.

The above-identified documents are incorporated herein by reference. While these applications have been incorporated by reference to provide additional detail it should be noted that these other applications were written at an earlier time and had a different focus from the present application. Thus, to the extent that the teachings or use of terminology differ in any of these incorporated applications from the present application, the present application controls.

BACKGROUND

Field of the Disclosure

This disclosure relates generally to orthopedics, and more particularly, to systems and methods for providing access to the spine to facilitate various implantation procedures. This disclosure includes teachings directed to use of radio-opaque markers to assist in placement of an access cannula while using fluoroscopic imaging equipment.

SUMMARY

A system for accessing a spine from a curved posterolateral approach may include a curved cannula positioned along a curved path from an opening in the skin to a location proximate the spine. The location may be at the L4-L5 vertebral level, and the curved path may lie in a plane oblique to the transverse, coronal, and sagittal planes of the spine, and avoid the iliac crest. A targeting post may be inserted adjacent the spine to determine the location, and a guide member may be inserted to establish the curved path. A micrometer assembly may adjust a cephalad-caudal displacement between the post and the guide member. One or more intermediate cannulas may be inserted over the guide member to dilate tissues prior to insertion of the main cannula. An interbody device may be implanted into an intervertebral space through the cannula.

The process may be facilitated through use of radio-opaque markers to indicate the position of a radiolucent cannula. Markers may be positioned to form a cross hair image in fluoroscopy to assist in cannula placement. Radio-opaque inserts placed in and extended beyond the curved access cannula may have radiolucent windows to allow viewing of the cannula's radio-opaque markers. An appropriately placed curved access cannula may be clamped to prevent subsequent movement. Appropriate tools may be introduced through the curved access cannula and the distal radio-opaque tool heads may be viewed relative to the radio-opaque markers. The curved access cannula may be attached to the spine through one or more screws.

This summary is meant to introduce the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features, and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The figures provide a framework for discussing the various teachings of the present disclosure and are not intended to provide an exhaustive set of templates of the various ways that teachings of the present disclosure may be used. The components in the figures are not necessarily to scale, emphasis instead being placed upon illustrating the principles of the disclosure. Moreover, in the figures, like reference numerals designate corresponding parts throughout the different views.

FIG. 28A and FIG. 28B show a marker image corresponding to a cannula with an exit point directed posteriorly rather than laterally.

FIG. 29A and FIG. 29B show a marker image corresponding to a cannula rotated relative to the disc transverse midline.

DETAILED DESCRIPTION

The present disclosure relates to systems and methods for accessing intervertebral space and inserting spine implants between vertebral bodies. Those of skill in the art will recognize that the following description is merely illustrative of the principles of the disclosure, which may be applied in various ways to provide many different alternative embodiments. This description is made for illustrating the general principles of the teachings of this disclosure invention and is not meant to limit the inventive concepts in the appended claims.

The present disclosure teaches access to the spine through the use of postero-lateral approaches. A minimally invasive dilation and/or access device employing such an approach would have significant advantages in spinal orthopedic procedures over the lateral and anterior approaches. These advantages may include avoiding the need to turn the patient during surgery, less muscle retraction, less blood loss, less operating room time, minimized damage to the vascular system, organs, nerves and muscles, faster recovery, and an improved overall outcome for the patient.

Figure 1:
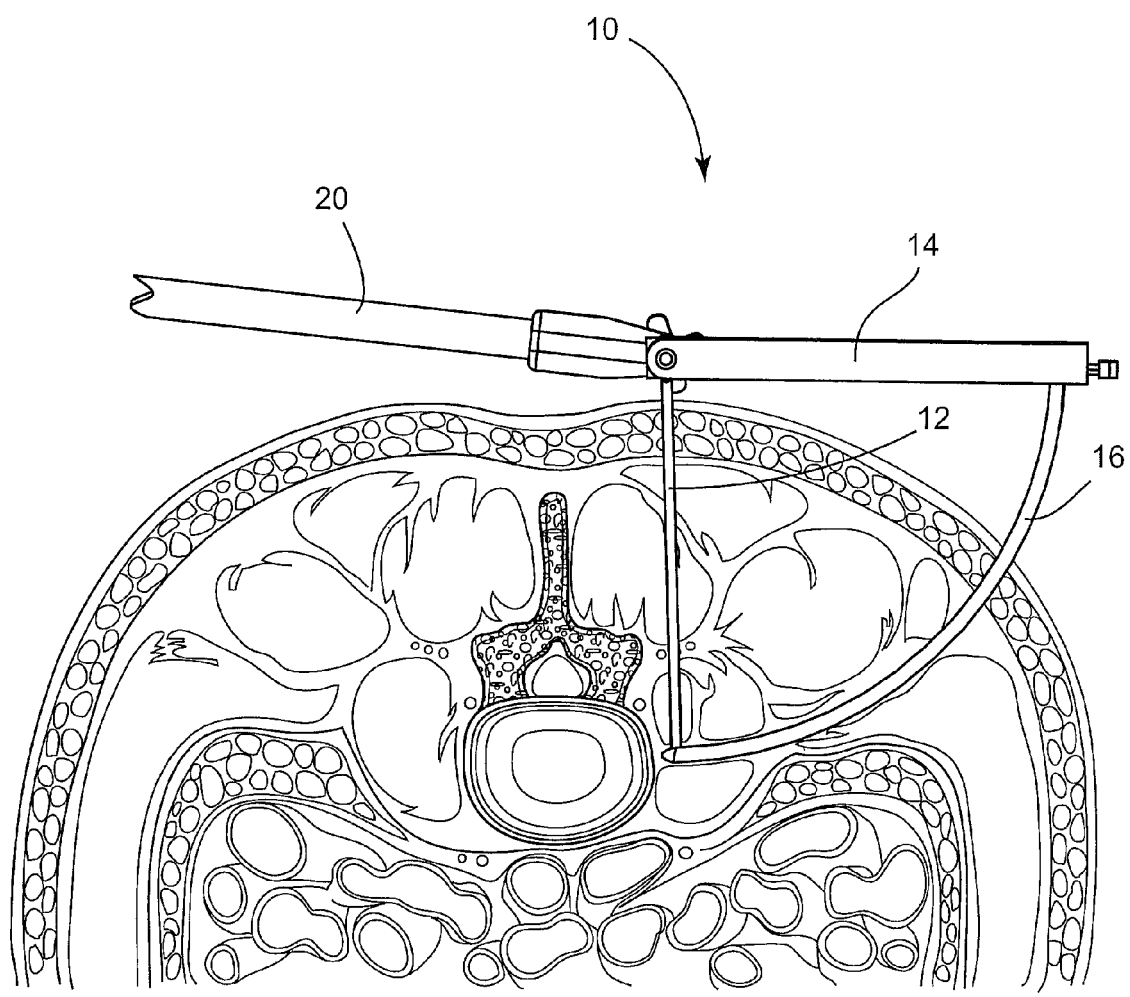
FIG. 1 is a cephalad view of a cross-section of a portion of a patient with an arcuate cannula assembly deployed adjacent a portion of the spine.

Referring to FIG. 1, one embodiment of an arcuate cannula assembly 10 is shown. The assembly 10 includes a targeting post 12, a guide arm 14, and a curved penetrating guide member 16 (for short-simply guide member 16). An instrument support arm 20 holds the assembly 10 and connects to an operating table (not shown). The assembly 10 may further comprise a series of graduated curved cannulas (not shown in FIG. 1), which are introduced sequentially over the guide member 16 to create access to a targeted portion of a spine. Use of the arcuate cannula assembly 10 creates an access portal to the intervertebral disc space or any element of the anterior spinal column through an arcuate path, from a postero-lateral approach.

The access portal is an unimpeded passage through which surgical instruments, implants and other materials may be passed to complete a variety of intervertebral procedures. This arcuate postero-lateral approach may be advantageous in performing a number of procedures, including but not limited to: implantation of motion preservation devices, total disc replacement, implantation of interbody devices, discectomy, lateral plating with or without dynamic elements, vertebra fixation or graft compression using plates or staples, foraminotomy, decompression, annulotomy, nucleotomy, annulus or nucleus repair, vertebral body biopsy, vertebroplasty, height restoration of a collapsed vertebral body (vertebral body augmentation), implantation of a fusion cage with stabilization features, implantation of a fusion cage with teeth to hold endplates together, or implantation of a curved or straight staple across the disc space to provide compression on the cage and stabilization of the cage.

Figure 2:
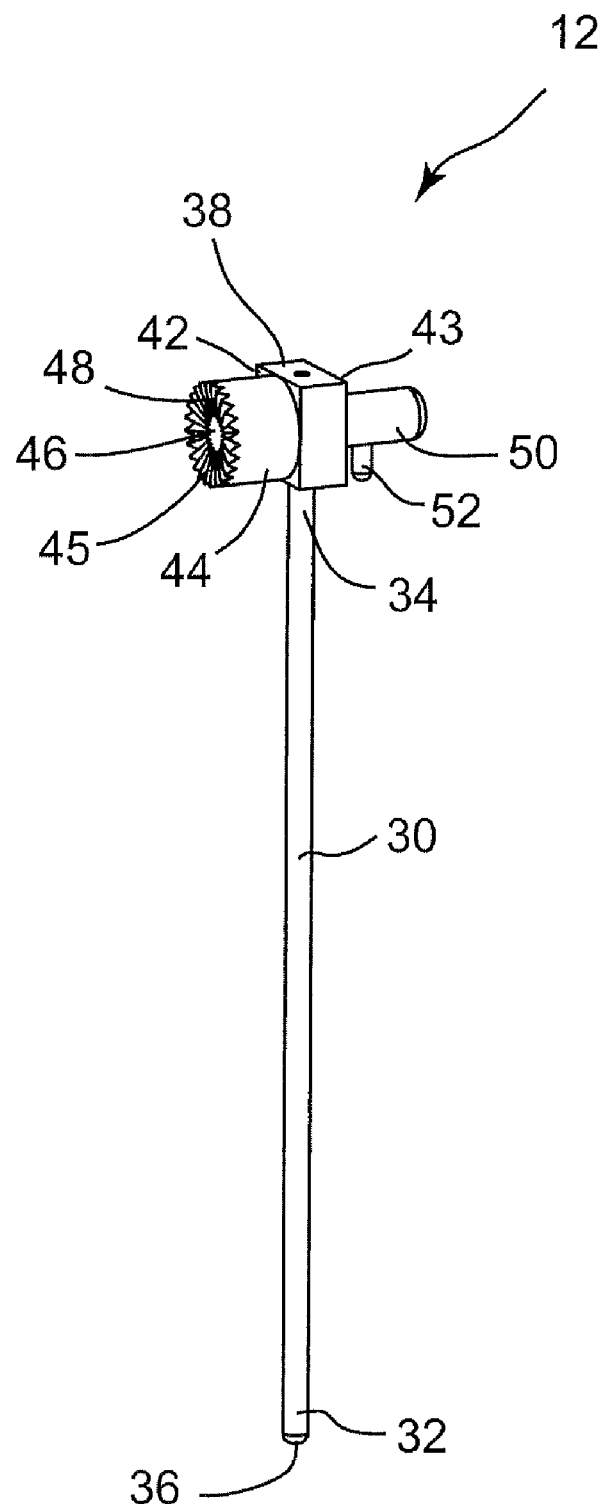
FIG. 2 is a perspective view of a targeting post of the arcuate cannula assembly of FIG. 1.

Referring to FIG. 2, a perspective view of the targeting post 12 is shown. The targeting post 12 includes an elongated shaft 30 with a distal end 32 and a proximal end 34. A rounded tip 36 is at the terminus of the distal end 32. The proximal end 34 adjoins a rectangular connector block 38 which has a first side 42 and a second side 43. Adjoining the connector block 38 on the first side 42 is a support arm attachment post 44. The attachment post 44 has a receiving slot 46 which extends transversely into the attachment post through an interface surface 45.

In one embodiment, the receiving slot 46 includes an internally threaded surface. A radial spline 48 encircles the receiving slot 46 on the interface surface 45. Adjoining the connector block 38 on the second side 43 is a rotation post 50. Extending distally from the rotation post 50 is an optional stop feature 52. An alternative embodiment may include a targeting post with a polyaxial joint, enabling the support arm 20 and/or guide arm 14 to be oriented at an angle relative to the targeting post.

Figure 3:
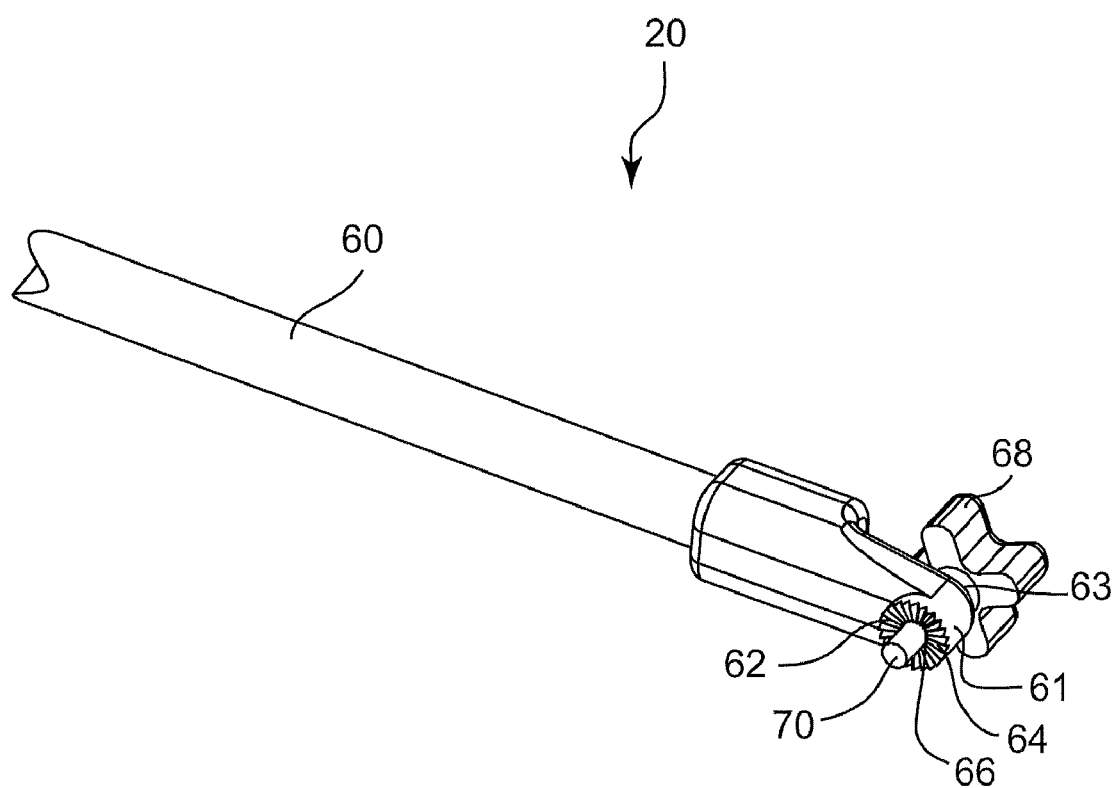
FIG. 3 is a perspective view of a portion of an instrument support arm.

Referring to FIG. 3, a perspective view of a support arm 20 is shown. The support arm 20 includes a shaft 60 which attaches to the operating table via various linkages, pivots, or connections to allow multiple degrees of freedom to accommodate the positioning of the instrument to be held. A wide variety of differently-configured instrument support arms are well known in the art and the assembly 10 (FIG. 1) may be compatible with the instrument support arm of choice for the surgeon.

A distal end 61 of the shaft 60 has a first side 62 and a second side 63. Extending transversely through the distal end 61 from the first side 62 to the second side 63 is a screw channel 66. On the first side 62, an interface surface has a radial spline 64 which encircles the opening of the screw channel 66. The radial spline 64 is configured to mate with the radial spline 48 on the targeting post 12 (FIG. 2) when the post is connected to the support arm 20. Extending through the channel 66 is a thumb screw 68, and a shaft 70 protrudes from the channel 66 on the first side 62. In one embodiment, shaft 70 includes an externally threaded surface configured to interface with the threaded receiving slot 46 on the targeting post 12.

Figure 4:
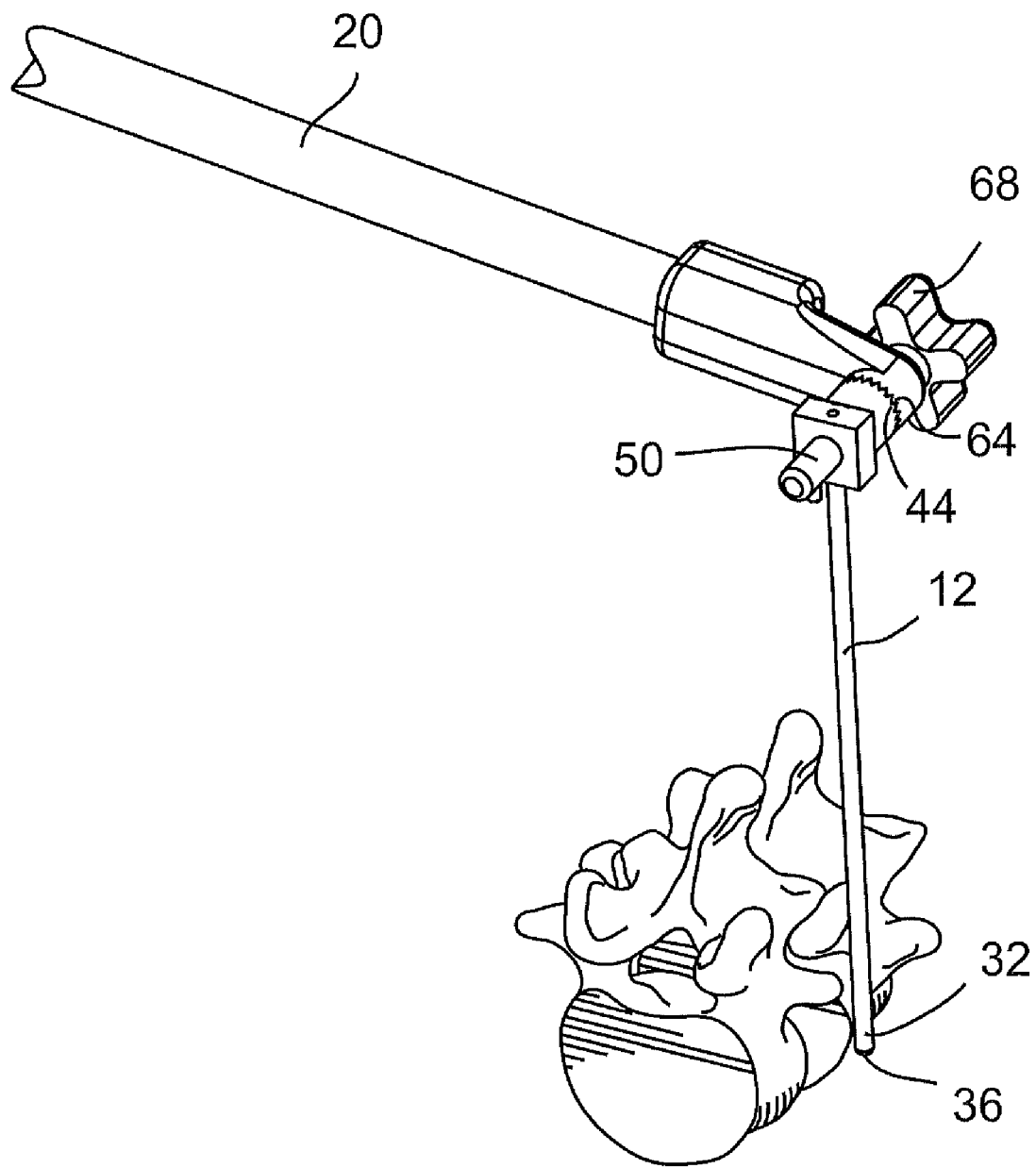
FIG. 4 is a perspective view of the instrument support arm of FIG. 3 supporting the targeting post of FIG. 2 adjacent a portion of a spine.

Referring to FIG. 4, the targeting post 12 is introduced into the patient from a postero-lateral approach through a small incision on the patient's back posterior to the targeted spine segment. The distal end 32 of the targeting post 12 is advanced antero-medially through the patient just lateral to the targeted intervertebral disc until the tip 36 reaches a desired reference location at the anterior lateral half or one third of the disc. The blunt shape of the tip 36 gently pushes tissues aside as the post 12 is advanced in. The post 12 may also be wired as an electrode during insertion, allowing for nerve monitoring or electromyography (EMG) to avoid nerves as the post 12 advances through the tissues. Of special concern is avoidance of the nerve roots exiting the spinal column as the psoas muscle adjacent to the spine is penetrated by the post 12. The targeting post 12 is inserted so that it is coplanar with the superior endplate of the inferior vertebral body for the intervertebral level to be treated. Preferably, the post 12 is aligned parallel with the sagittal plane of the patient, but other orientations are possible if necessary to avoid nerves or other obstacles. The targeting post 12 may be available in a variety of lengths to accommodate patients of differing proportions, and to reach specific reference locations.

When the distal end 32 of the targeting post 12 has reached the reference location, the proximal end 34 (FIG. 2) is attached to the support arm 20 via the thumb screw 68. The protruding screw shaft 70 (FIG. 3) is threaded into the receiving slot 46 (FIG. 1). As the thumb screw 68 is threaded in, the radial splines 44, 64 mesh, locking the targeting post 12 to the support arm 20. Once attachment is made between the targeting post 12 and the support arm 20, the various degrees of freedom of the support arm 20 are locked down to provide sufficiently rigid instrument stabilization.

In position adjacent to the spine, the targeting post 12 acts as a stabilizing and reference guide for subsequent cannulas, instruments, and implants. The targeting post 12 may optionally be affixed to the patient to provide additional stability.

Figure 5:
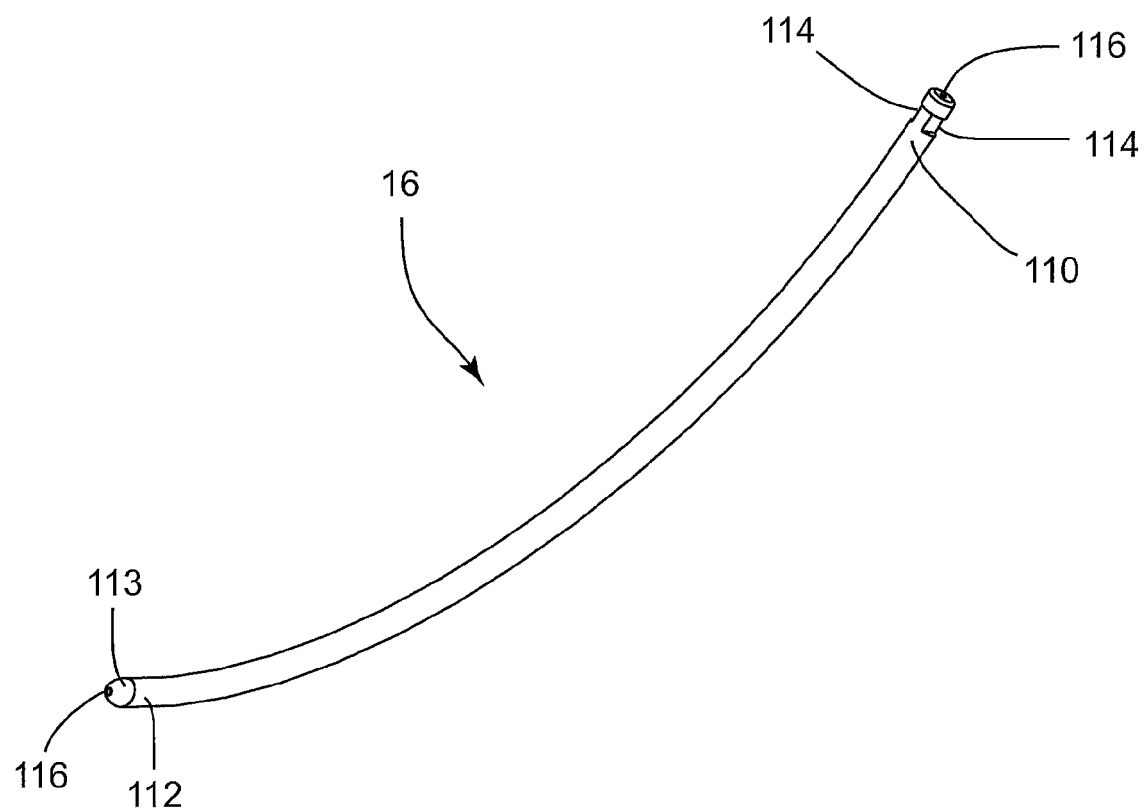
FIG. 5 is a perspective view of a guide member of the arcuate cannula assembly of FIG. 1.

Referring to FIG. 5, the penetrating guide member 16 is shown. The penetrating guide member 16 is curved and may be arcuate (i.e., may extend along a fixed radius of curvature). The penetrating guide member 16 has a proximal end 110, and a distal end 112 with an insertion tip 113. The insertion tip 113 may be rounded or optionally pointed, to penetrate muscles and fascia. Two attachment recesses 114 at the proximal end facilitate attaching the guide member 16 to the guide arm 14 (FIG. 1), and are configured to connect to an instrument support arm. A narrow channel may optionally extend the length of the penetrating guide member 16, sized to receive a wire for nerve monitoring or EMG during dilation.

Figure 6A:
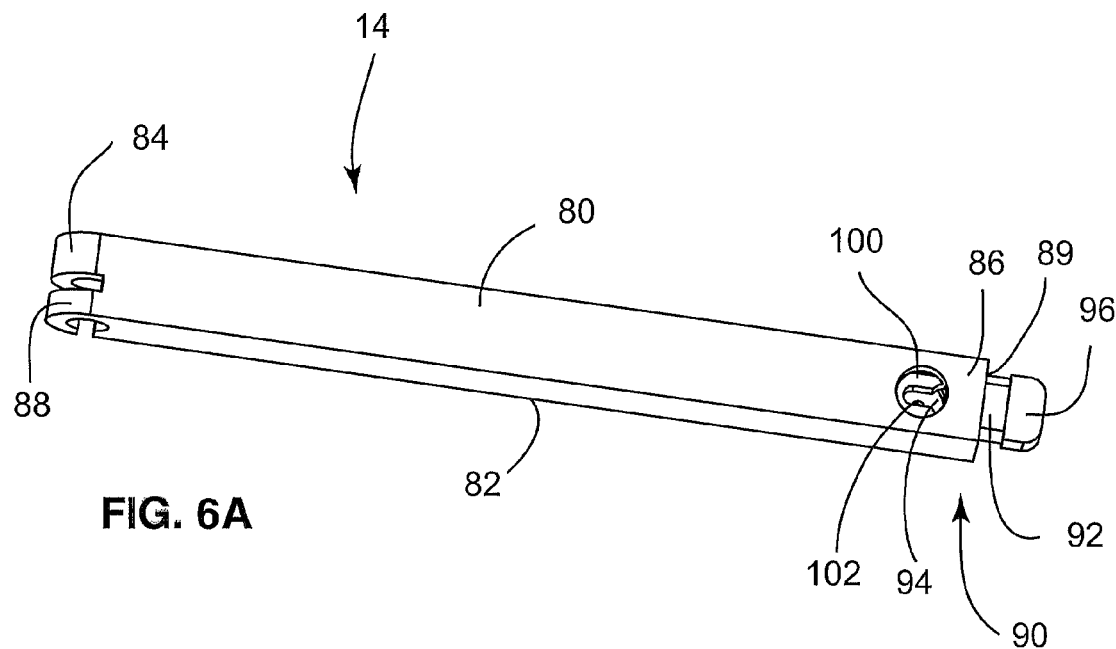
FIG. 6A is a perspective view of a guide arm of the arcuate cannula assembly of FIG. 1.

Referring to FIG. 6A, a perspective view of the guide arm 14 is shown. The guide arm 14 has a first side 80 and a second side 82. At a proximal end is a pinned end 84; a latch end 86 is at the opposite distal end. The pinned end 84 has an attachment feature 88 which is shaped to rotatably attach to the rotation post 50 on the targeting post 12 (FIG. 2).

Inserted into a horizontal slot 89 in the latch end 86 is a spring loaded guide member latch assembly 90 which is shaped to grip the penetrating guide member 16 (FIG. 1). The guide member latch assembly 90 has a sliding latch bar 92 with a keyhole 94 and a tab 96. On the first side 80 of the guide arm 14, near the latch end 86 is a round guide member opening 100. Directly opposite guide member opening 100 on the second side 82 may optionally be a smaller pinhole opening 102.

Figure 6B:
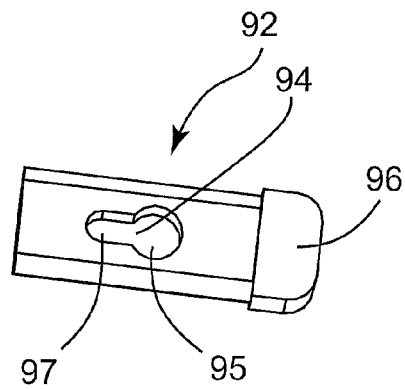
FIG. 6B is a perspective view of a sliding latch bar of the guide arm of FIG. 6A.

FIG. 6B is an enlarged view of the sliding latch bar 92. Keyhole 94 has a rounded lobe 95 disposed toward the tab 96, and an ovoid lobe 97 opposite the tab 96. The rounded lobe 95 is sized to fit around the proximal end 110 of the guide member 16 (FIG. 5). The ovoid lobe 97 is sized to hold the attachment recesses 114 of the guide member 16 (FIG. 5). The tab 96 may be grasped to move the sliding latch bar 92 within the horizontal slot 89. A spring (not shown) is disposed in the horizontal slot 89 to provide resistance against the sliding latch bar 92.

Figure 7:
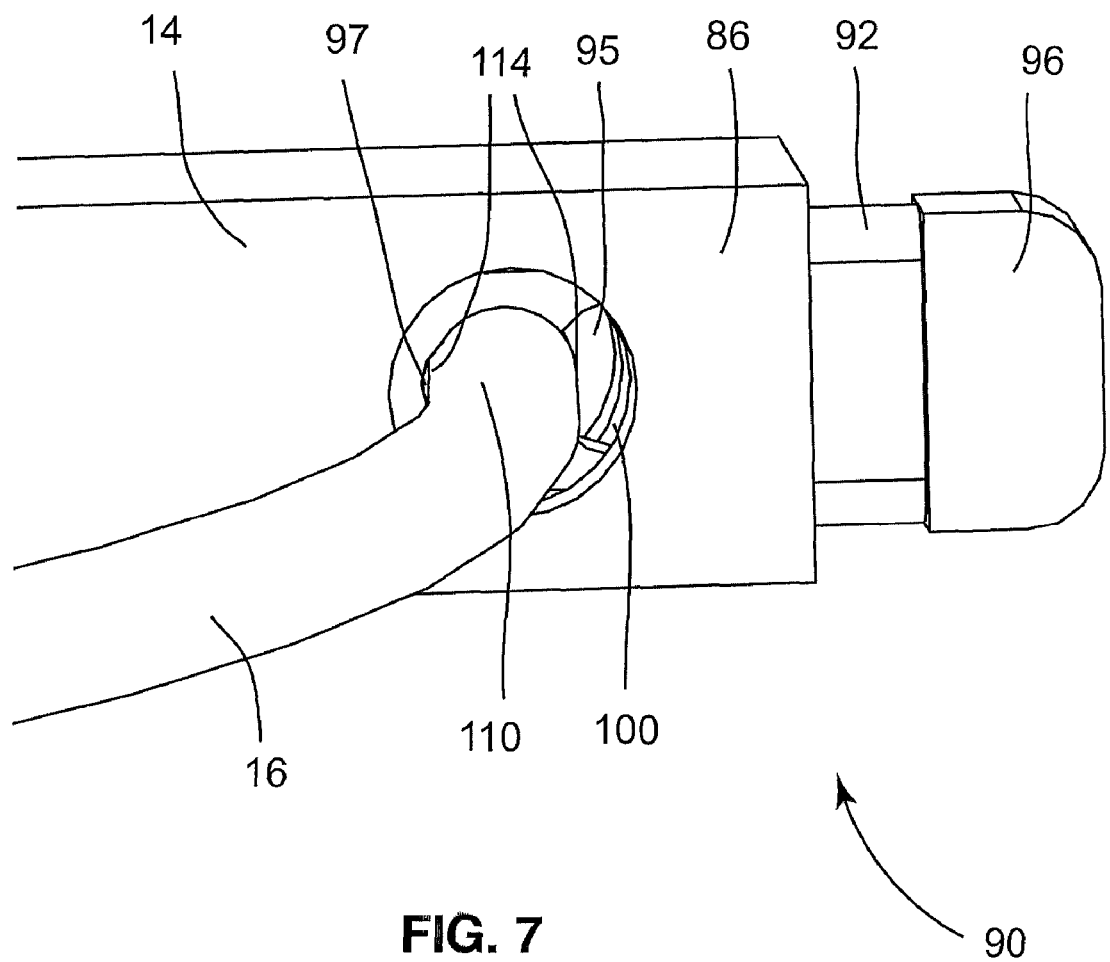
FIG. 7 is a perspective view of a latch assembly of FIG. 6A, with the guide member of FIG. 5 latched thereto.

FIG. 7 is an enlarged view of the latch end 86 of the guide arm 14, showing the guide member 16 latched in the latch assembly 90. To latch the guide member 16 in the latch assembly 90, first the sliding latch bar 92 is introduced into the horizontal slot 89 (FIG. 6A) until the rounded lobe 95 of the keyhole 94 (FIG. 6A) lines up with the guide member opening 100. The proximal end 110 of the guide member 16 is inserted such that the attachment recesses 114 are adjacent to the lined up keyhole 94 and opening 100. The sliding latch bar 92 is released, and the spring (not shown) pushes the sliding latch bar 92 distally until the ovoid lobe 97 of the keyhole 94 (FIG. 6B) slides around the attachment recesses 114 of the guide member 16. The force of the spring traps the guide member 16 in the latch assembly 90, as the guide member is pinned between the ovoid lobe 97 and the latch end 86 of the guide bar 14 adjacent the guide member opening 100.

Figure 8:
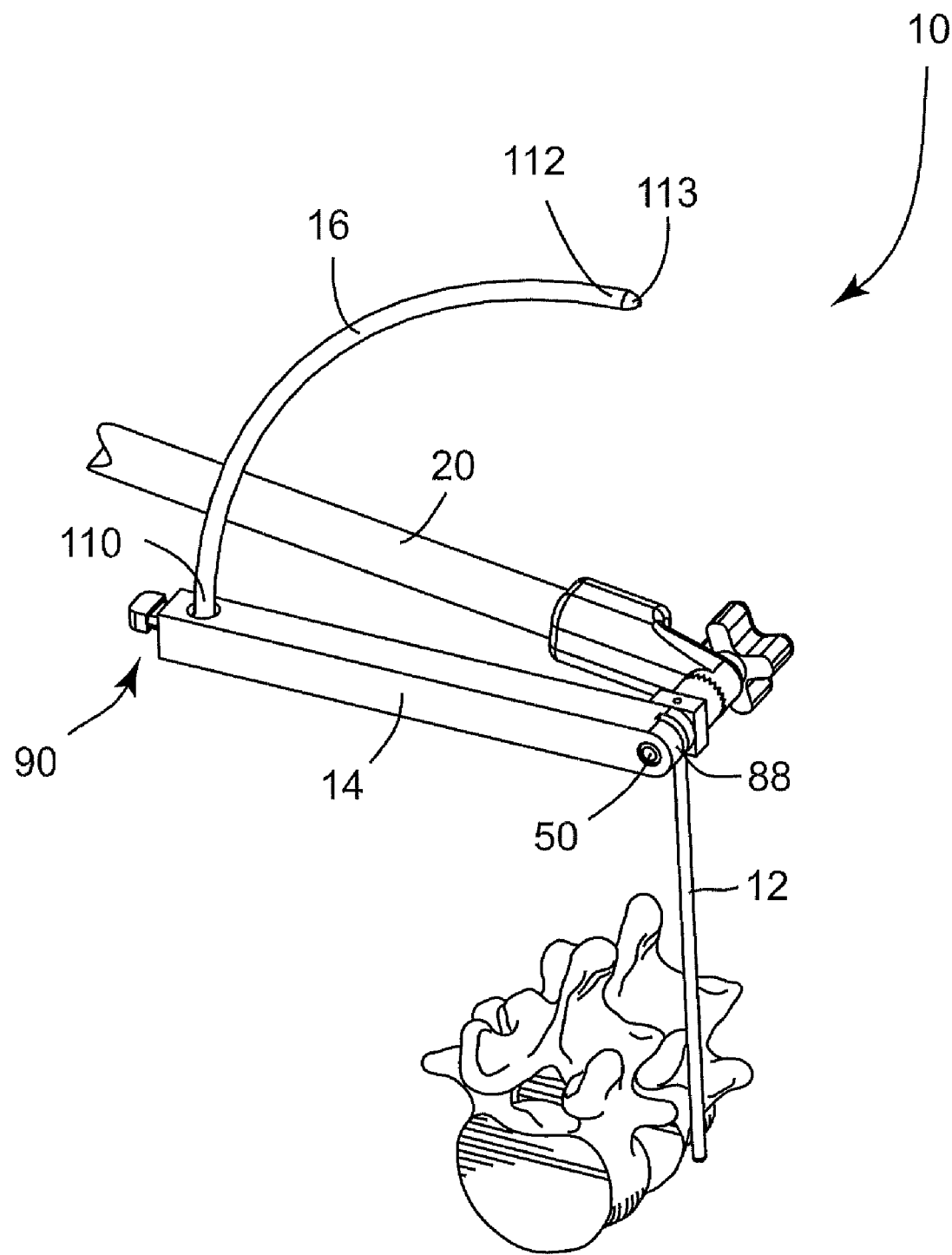
FIG. 8 is a perspective view of the arcuate cannula assembly of FIG. 1 with the guide arm in a first position, adjacent a portion of the spine.

Referring to FIG. 8, the support arm 20, targeting post 12, guide arm 14 and penetrating guide member 16 are shown, with the guide arm 14 and penetrating guide member 16 in a first position. The attachment feature 88 on the guide arm 14 is engaged with the rotation post 50 on the targeting post 12. Thus attached, the guide arm 14 can rotate about the axis of the rotation post 50; however the stop feature 52 (FIG. 2) on the rotation post 50 may prevent the guide arm 14 from rotating entirely about the rotation post 50.

The guide arm 14 may be sized to match the radius of the curve of the penetrating guide member 16, such that the arc center point of the penetrating guide member 16 is coincident with the center of rotation, or axis of the rotation post 50. The guide member latch 90 holds the penetrating guide member 16 as seen in FIG. 7.

After the penetrating guide member 16 is attached to the guide arm 14, the guide arm 14 is rotated so that the insertion tip 113 of the guide member 16 makes contact with the skin. Optionally, an incision location may be marked on the skin. At this point, the guide member 16 is lifted and an incision of approximately 1-5 cm is made into the skin and fascia. Following the incision, the surgeon may insert a finger into the incision to locate and palpate the soft tissues and fascia.

Figure 9:
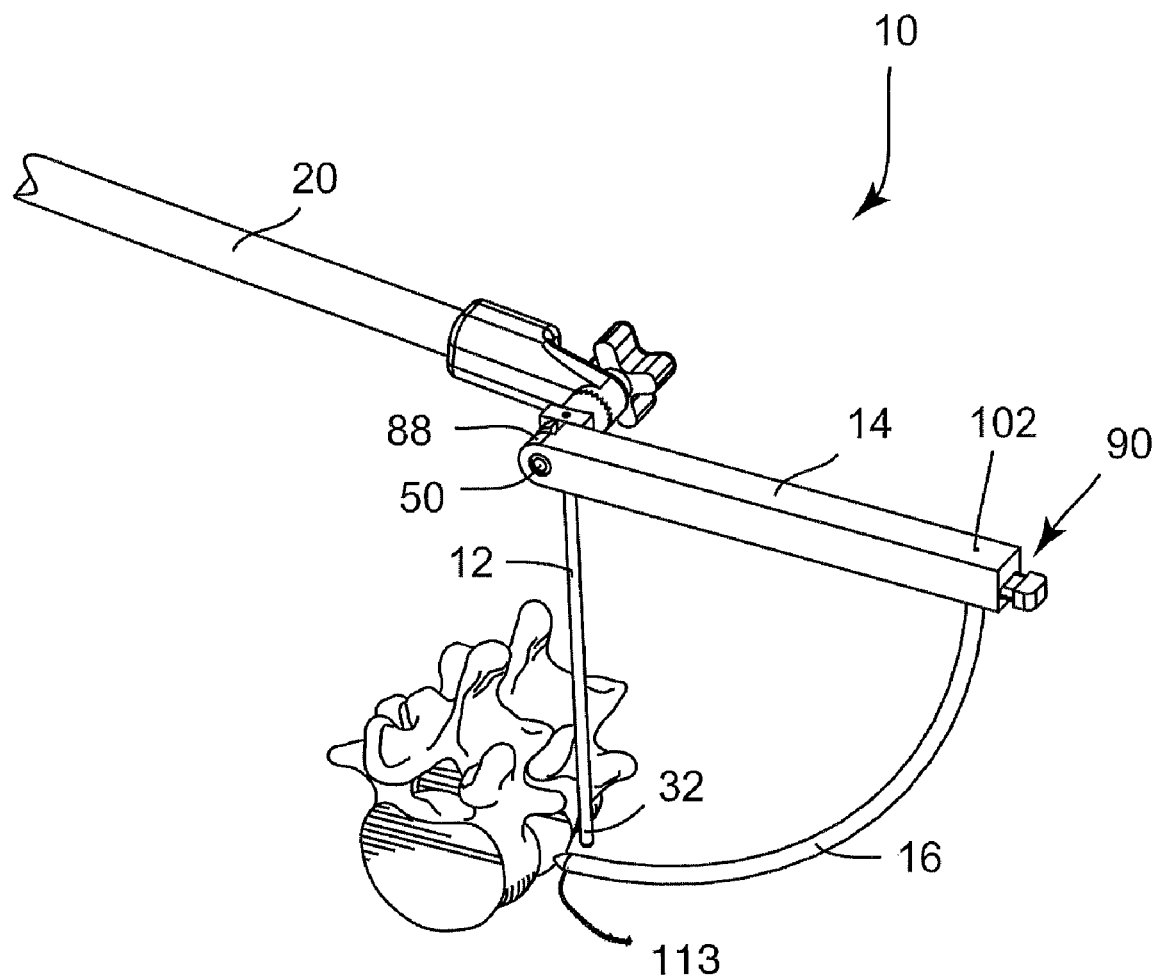
FIG. 9 is a perspective view of the arcuate cannula assembly of FIG. 1 with the guide arm in a second position, adjacent a portion of the spine.

As shown in FIG. 9, the guide member 16 is then advanced into the incision via rotation of the guide arm 14. The guide member 16 is advanced antero-medially along the arcuate path until the insertion tip 113 is at the lateral margin of the targeted disc, at a target location. The target location is at a known position relative to the reference location provided by the distal end 32 of the targeting post 12, as the guide arm 14 holds the guide member 16 in a fixed relationship as the guide arm 14 rotates about the rotation post 50.

At this point the guide arm 14 and guide member 16 are in a second position. The guide member 16 may have a rounded insertion tip, or a sharp, pointed insertion tip if necessary to penetrate the tissues. EMG monitoring may be used to ensure safe passage of the guide member 16 through the fascia. The optional pinhole opening 102 creates access for a wire to pass through the guide arm into the guide member 16 if it is desirable to connect an electrode to the guide member 16 for nerve monitoring.

The stop feature 52 (seen in FIG. 2) stops rotation of the guide arm 14 and prevents the guide member 16 from extending past the margin of the disc and contacting the spinal cord. The penetrating guide member 16 may vary in length and radius of curvature, to accommodate differing patient proportions and differing specific target locations. Accordingly, the guide arm 14 may be adjustable in length, to function correctly with the guide member 16 to reach the target location.

Once the guide member 16 is correctly positioned adjacent the targeted location, the guide arm 14 is detached from the guide member 16 and the targeting post 12. The guide member 16 is left in the patient to serve as a guide for one cannula or series of cannulas which may be graduated in size, and which are inserted sequentially from smaller to larger to increase the cross-sectional area of the access portal to the area to be treated.

Figure 10:
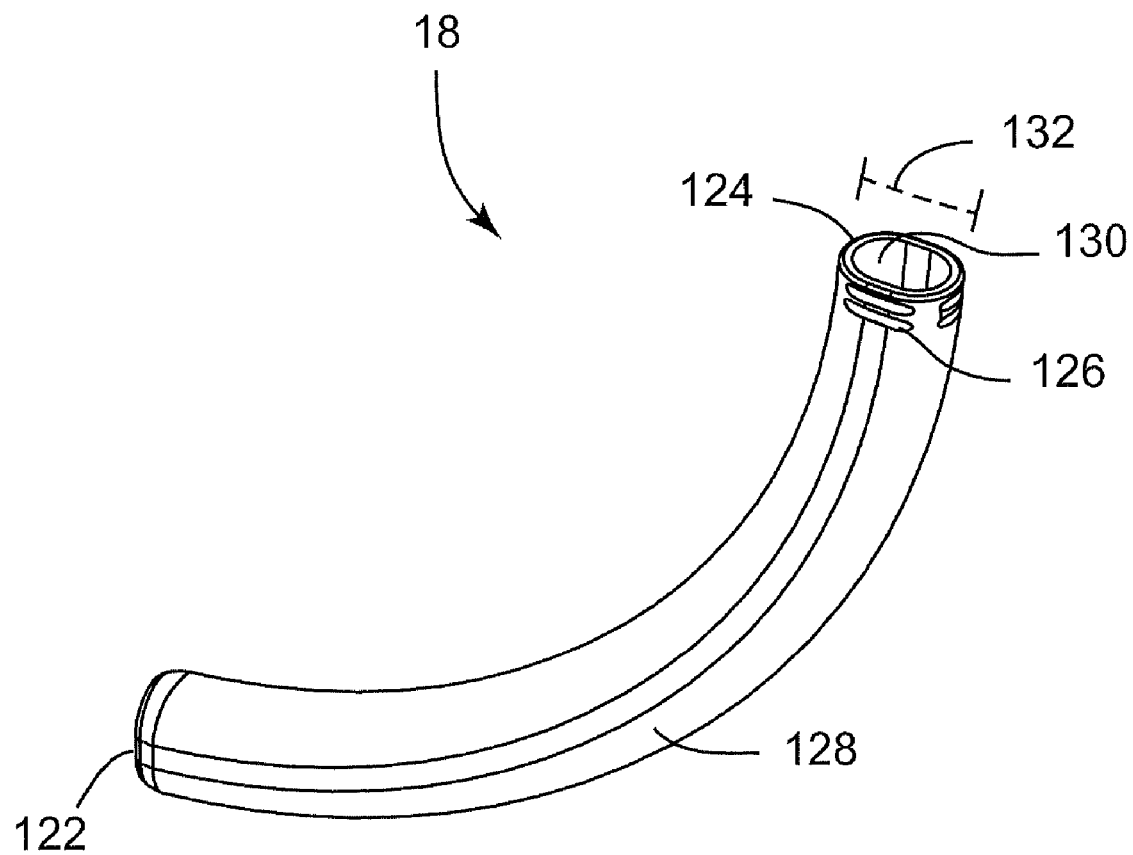
FIG. 10 is a perspective view of a cannula.

Referring to FIG. 10, a single cannula 18 is shown. The cannula 18 is longitudinally curved and generally tubular in form, with a tubular support wall 128 which has an open distal end 122 and an open proximal end 124. The distal end 122 may be rounded so that tissues are pushed aside gently as the cannula is inserted through the patient. A bore 130 runs the length of the cannula 18 from the open distal end 122 to the open proximal end 124, and provides access to the targeted spinal area for instrument insertion, and insertion and removal of interbody devices, arthroscopic devices, implants, bone graft materials, bone cement, and other materials and devices. A cross-sectional shape of the support wall 128 of the bore 130 is generally curved, and may specifically be round, oval, elliptical or another curved shape. The cross-sectional shape has a width 132, which may have a maximum measurement of about 27 millimeters.

The open proximal end 124 has a plurality of grip features 126 which allow the surgeon to grip the cannula. Optionally, the cannula 18 may have attachment features to allow attachment of the cannula to the instrument support arm. The cannula 18 may optionally be substantially radiolucent, and can comprise biocompatible polymers, elastomers, ceramics, or aluminum or other metals. The longitudinal curve of the cannula 18 may be arcuate, and may sweep through an angle of about 90 degrees such that the open proximal and distal ends 124, 122 are substantially perpendicular to each other. A radius of curvature of the cannula may be constant along the entire cannula, and may range from about 2 to about 9 inches.

Figure 11:
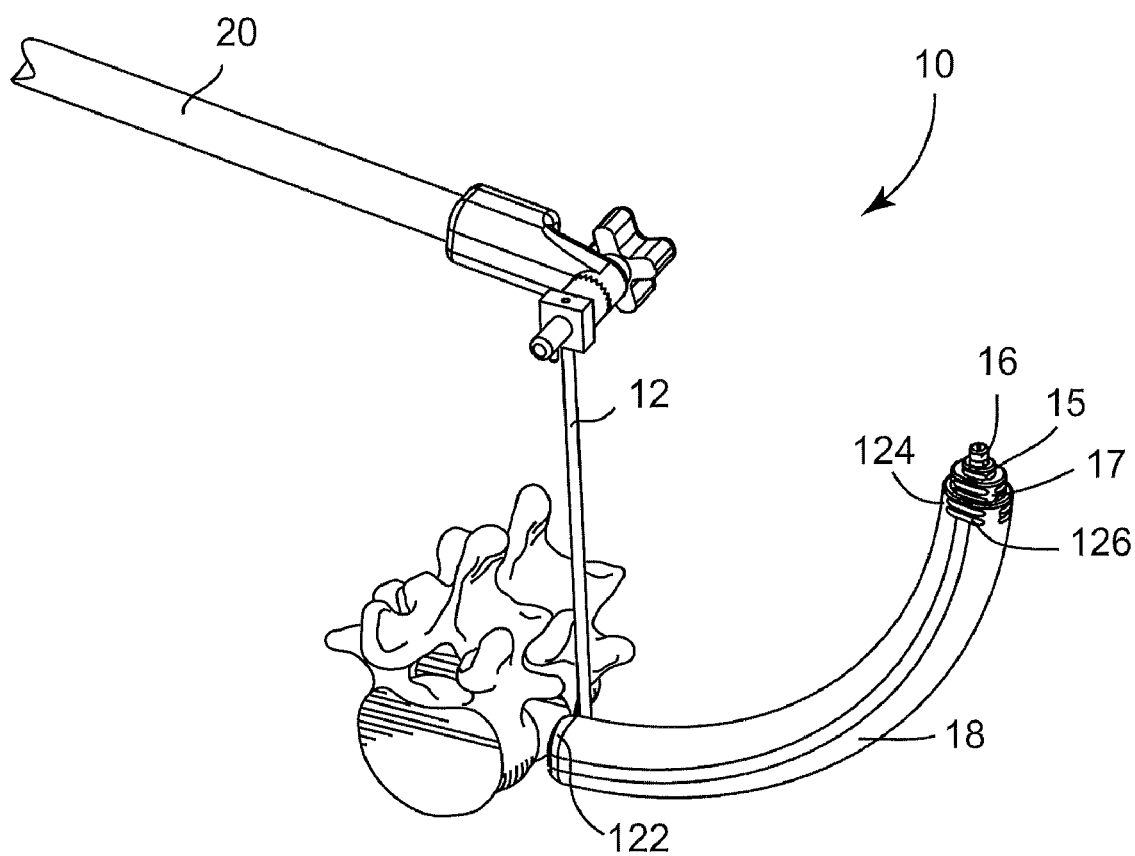
FIG. 11 is a perspective view of the arcuate cannula assembly of FIG. 1 with the guide arm removed and several cannulas added, adjacent a portion of the spine.

Referring to FIG. 11, a series of graduated cannulas 15, 17, 18 are inserted one at a time over the proximal end 110 (FIG. 5) of the penetrating guide member 16, and advanced antero-medially over the guide member 16 until the corresponding distal end reaches the distal end 112 (FIG. 5) of the guide member 16. Each cannula 17, 18 may be shorter in length and larger in cross-sectional area than the next smallest cannula, to allow the surgeon to grip each cannula as it is installed and removed. As each cannula 15, 17, 18 is inserted, the access portal through the soft tissues and fascia is increased in size, creating increased access to the targeted portion of the spine.

The number of cannulas inserted is determined by the desired cross-sectional area of the opening to the spine; in many instances two to five cannulas will be inserted. Once all cannulas 15, 17, 18 are inserted around the penetrating guide member 16, the guide member 16 and the inner cannulas 15, 17 are removed, leaving the largest cannula 18 in the patient. This largest cannula may be attached via an attachment feature (not shown) to the support arm 20, to provide additional stabilization for removal of the smaller cannulas, and for subsequent instrument insertion and procedures. In the embodiment depicted, the penetrating guide member and all cannulas sweep through an angle of about 90 degrees. It is appreciated that in alternate embodiments, the penetrating guide member and all cannulas may sweep through an angle from at least 45 degrees to 135 degrees.

In one embodiment, the largest cannula 18 may have a tooth portion (not shown) which extends longitudinally from the insertion end 122. During insertion, the tooth portion is placed between the superior and inferior endplates of the intervertebral space, to assist in maintaining distraction and access to the space. In an alternative embodiment, the largest cannula 18 may have one or more protruding pins or other elements extending from the insertion end 122 which can penetrate the superior and/or inferior vertebral bodies to provide additional stability to the cannula 18.

Figure 12:
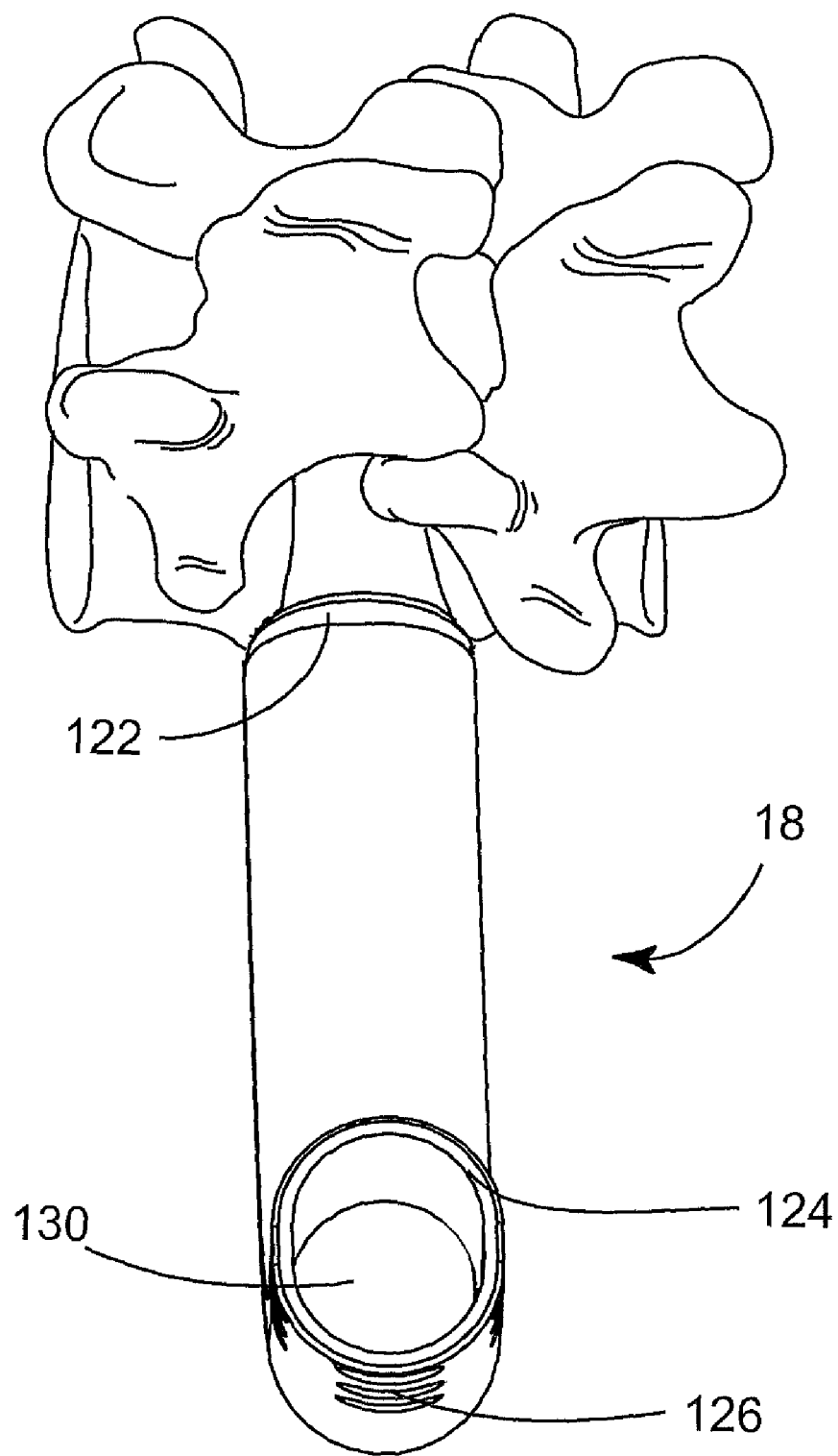
FIG. 12 is a postero-medial perspective view of the cannula of FIG. 10 adjacent a portion of the spine.

FIG. 12 is a postero-lateral view of a portion of a spine with a cannula inserted according to the procedure previously described. When in place in the patient, the bore 130 of the cannula 18 is an access portal through which surgical instruments, implants and other materials may be passed to complete a variety of intervertebral procedures. Surgical instruments used in conjunction with the cannula 18 may have rigid, curved shafts or flexible shafts to navigate through the cannula 18 to the intervertebral space. The cannula 18 may be sized to accommodate passage of an interbody fusion implant or other implant.

Another embodiment of the disclosure includes a targeting post which is capable of cephalad-caudal adjustment.

Figure 13:
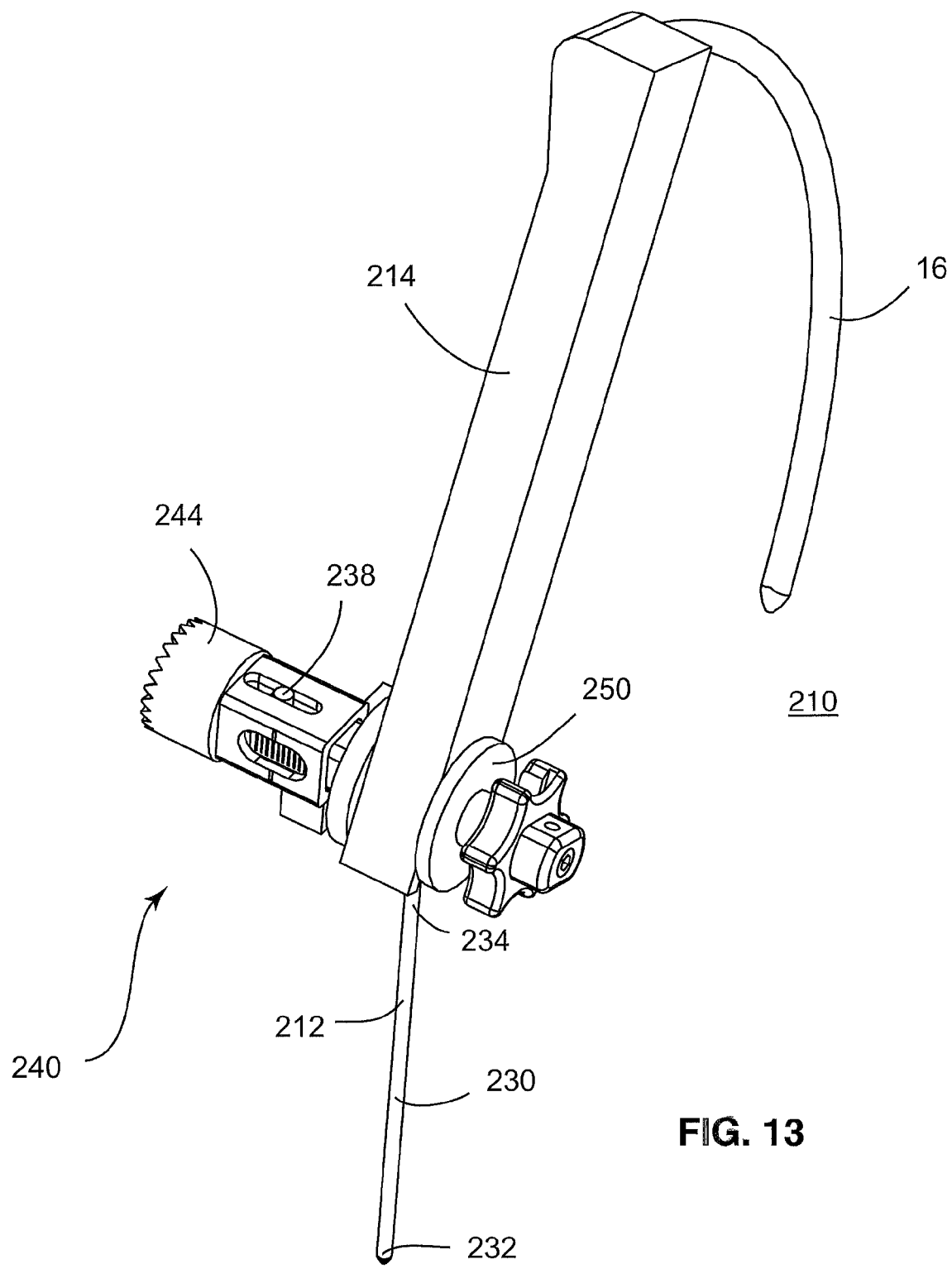
FIG. 13 is a perspective view of an arcuate cannula assembly with an adjustable targeting post.

FIG. 13 is a perspective view of an arcuate cannula assembly 210 which includes an adjustable targeting post 212, a guide arm 214 and a penetrating guide member 16. The adjustable targeting post 212 has a shaft 230 which has a distal end 232 and a proximal end 234. Proximally adjacent to the proximal end 234 of the shaft 230 is a connection portion 240, which extends in a cephalad-caudal direction and includes a guide arm connector 250, a cephalad-caudal adjustment feature 238, and a support arm attachment post 244. The cephalad-caudal adjustment feature 238 can be adjusted to lengthen or shorten the cephalad-caudal length of the connection portion 240.

Thus, after the targeting post 212 is inserted into the patient, the length of the connection portion 240 can be adjusted as necessary to attain the necessary offset to adjust the resultant cephalad-caudal distance between the penetrating guide member 16 and the targeting post 212. The adjustment allows the target location to vary along the cephalad-caudal direction such that the known position of the target location is offset relative to the reference location. Cephalad-caudal offset of the guide arm 214 and the attached guide member 16 may be useful in avoidance of nerve structures and other objects during the dilation process.

Another application of the disclosure includes a bilateral implementation of two arcuate cannula assemblies. In this embodiment, two assemblies 10 are used together, one on each lateral side of the spine.

Figure 14:
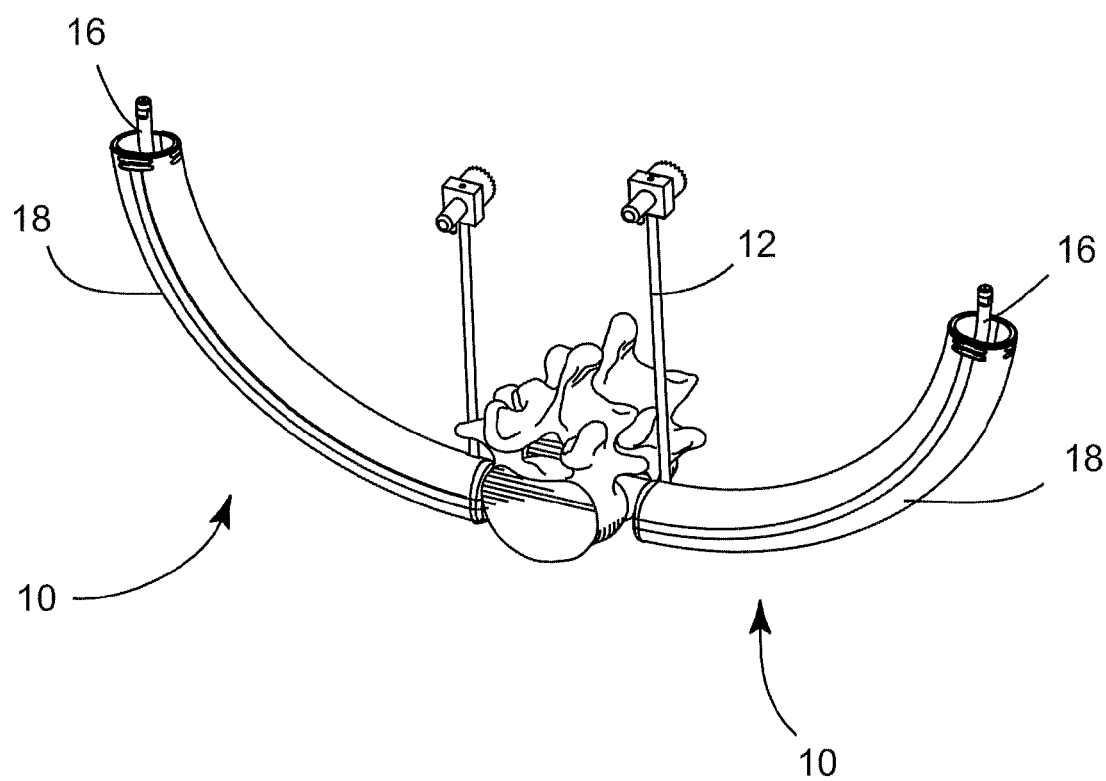
FIG. 14 is a perspective view of two arcuate cannula assemblies of FIG. 1, adjacent two lateral sides of a portion of the spine.

Referring to FIG. 14, portions of two assemblies 10, two targeting posts 12, two penetrating guide members 16, and two cannulas 18, are shown adjacent to each lateral side of the spine. This embodiment permits enhanced access to the targeted area, since access may be attained from both lateral sides simultaneously. Instruments, implants, or other materials may be pushed or pulled into the intervertebral space, or through the entire access pathway.

Figure 15A:
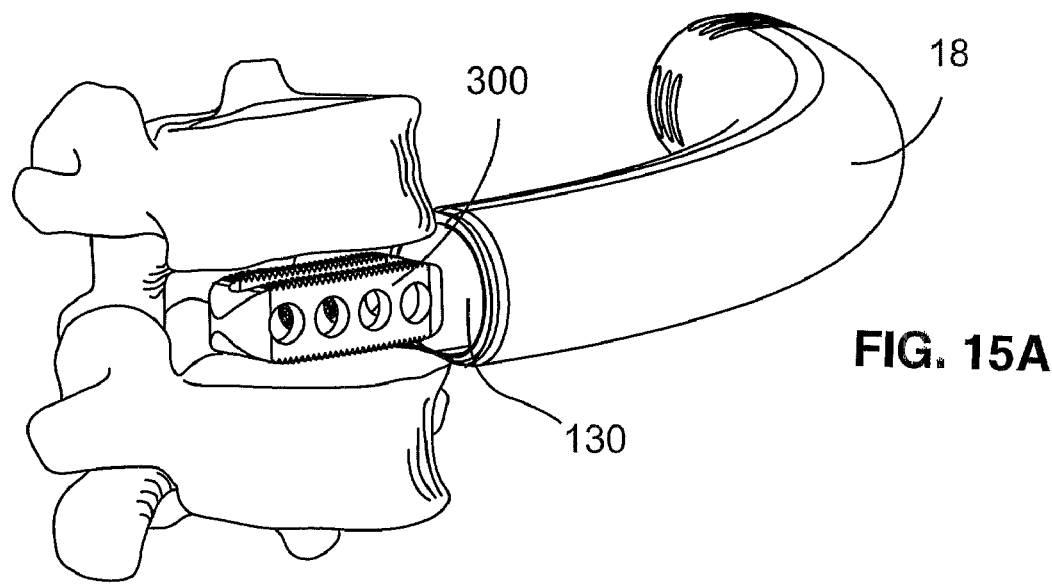
FIG. 15A is an antero-medial perspective view of the cannula of FIG. 10 adjacent a portion of a spine, and an interbody device in an intervertebral space.

Another teaching of the present disclosure includes an implant, which may be an interbody device. FIG. 15A is an anterior perspective view of first and second vertebrae with a cannula 18 and one type of implant, specifically, an interbody device 300 which may be inserted through the arcuate cannula assembly previously disclosed. An implant retaining inserter with a curved shaft (not shown) may be used to move the implant along the arcuate pathway of the cannula, then release the implant in the interbody space between the vertebrae.

Figure 15B:
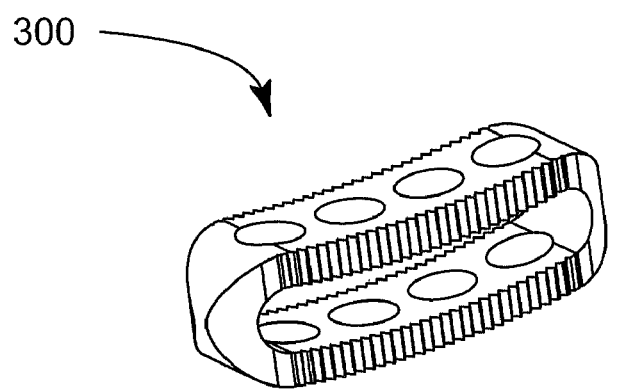
FIG. 15B is a perspective view of the interbody device of FIG. 15A.

FIG. 15B is a perspective view of the interbody device 300 of FIG. 15A. The interbody device 300 shown in FIG. 15B has a generally rectangular box-like shape, and is slightly curved along its longitudinal axis. The interbody device 300 may optionally have a radius of curvature substantially the same as that of the cannula 18.

Other implants (not shown) may be shaped to be implantable through the cannula in the manner set forth previously and illustrated in FIG. 15A. These implants may include, but are not limited to, a nucleus replacement, an annulus replacement, a staple, a lateral plate, a lateral plate-interbody implant combined device, an artificial disc, a therapeutic-containing implant, a vertebral body screw, a vertebral body anchor, and a facet replacement.

In any case, the bore 130 (FIG. 15A) of the cannula 18 is sized to accommodate passage of the interbody device 300. Because use of the arcuate cannula assembly 10 allows improved access to the intervertebral space, the interbody device 300 may have a larger footprint than many other interbody devices, and can extend across most of the medial-lateral width of the intervertebral space, to provide for increased stability, increased bone in-growth, and improved fusion. A curved insertion tool and curved tamp (not shown) are used to insert and seat the interbody device 300 in the intervertebral space. In the alternative, a flexible insertion tool and/or a flexible tamp may be used.

A set of curved spinal orthopedic instruments may be used in conjunction with the arcuate cannula assembly set forth previously to complete spinal procedures. These instruments may include rasps, curettes, rongeurs, wedge distractors, trial implants, tamps, probes, and implant insertion devices, among others. Each instrument may have a gripping portion, and a working portion which includes a shaft and a specific tool portion, or working end. The shaft may be an arcuate shaft which extends along an arcuate shaft pathway that matches the pathway along which the corresponding cannula extends. The working end of each instrument is sized to pass through the arcuate cannula 18, and may be coupled to the arcuate shaft such that the working end follows the same trajectory as the arcuate shaft; thus the entire working portion may be continuously curving along the arcuate shaft pathway. The radius of curvature of the arcuate shaft pathway may substantially equal the radius of curvature of the arcuate cannula 18. Thus configured, the working portion of each instrument may be inserted through the arcuate cannula, allowing the working end to protrude out of the distal end of the cannula to reach the location of the spinal procedure.

Figure 16:
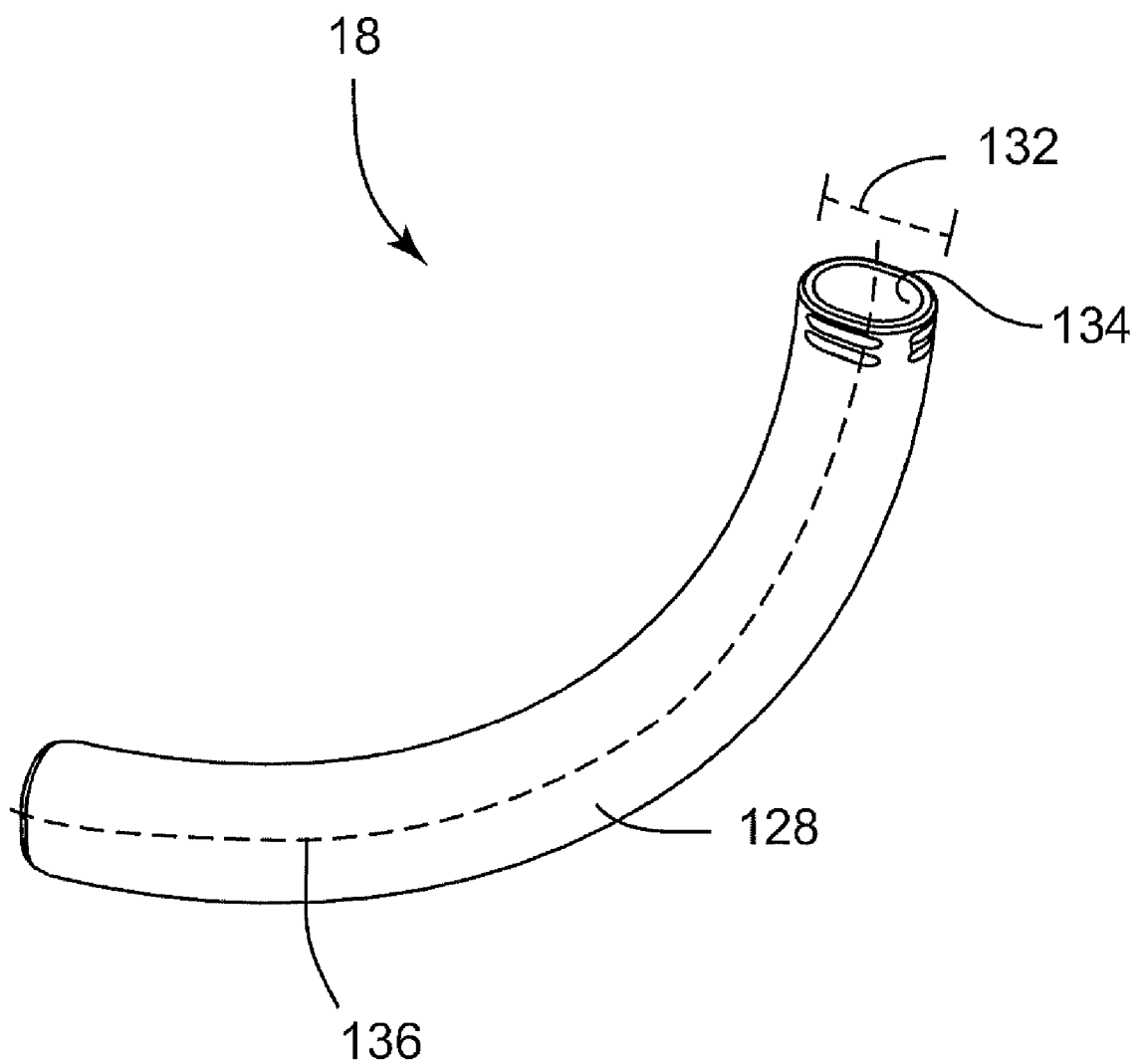
FIG. 16 is a perspective view of the cannula of FIG. 10, showing the boundaries of an arcuate envelope.

Referring to FIG. 16, a perspective view of the cannula 18 is shown. The cannula 18 is curved, and, as embodied in FIG. 16, is also arcuate. Thus, the cannula 18 defines an arcuate envelope through which an instrument may pass. The cannula 18 (and thus the arcuate envelope) extends longitudinally along an arcuate envelope pathway 136, which may have a radius ranging from about 2 inches to about 12 inches. More precisely, the arcuate envelope pathway may have a radius ranging from about 4 inches to about 9 inches. Still more precisely, the arcuate envelope pathway may have a radius of about 5.5 inches. The support wall 128 which forms the cannula has an interior surface 134. As mentioned previously, the interior surface 134 defines the arcuate envelope. The arcuate envelope, and thus the cannula 18, extends longitudinally along the arcuate envelope pathway 136, and may sweep through an arc ranging from about 45 to about 135 degrees. More precisely, the cannula 18 may sweep through an arc ranging from about 60 to about 120 degrees. Yet more precisely, the cannula 18 may sweep through an arc ranging from about 75 to about 105 degrees. Still more precisely, the cannula 18 may sweep through an arc of about 90 degrees.

The cannula 18 (and hence the corresponding envelope) has a substantially uniform cross-sectional shape, which may be circular, ovoid, elliptical or any other uniform, closed shape. A "substantially uniform cross-sectional shape" is possessed by an "extrusion," i.e., a body that extends along a pathway with substantially the same cross-sectional shape and size (taken perpendicular to the pathway) at any location along the length of the pathway. The maximum width of the arcuate envelope, defined as a straight line across the largest dimension of the cross-section taken at right angles to the arcuate envelope pathway 136, may range from about 5 millimeters to about 50 millimeters. More precisely, the maximum width may range from about 15 millimeters to about 40 millimeters. Yet more precisely, the maximum width may range from about 20 millimeters to about 30 millimeters. Still more precisely, the maximum width of the arcuate envelope may be about 27 millimeters. The arcuate shaft and working end of each instrument are configured and coupled together such that they may pass through the arcuate envelope and the working end may extend out of the envelope.

Figure 17:
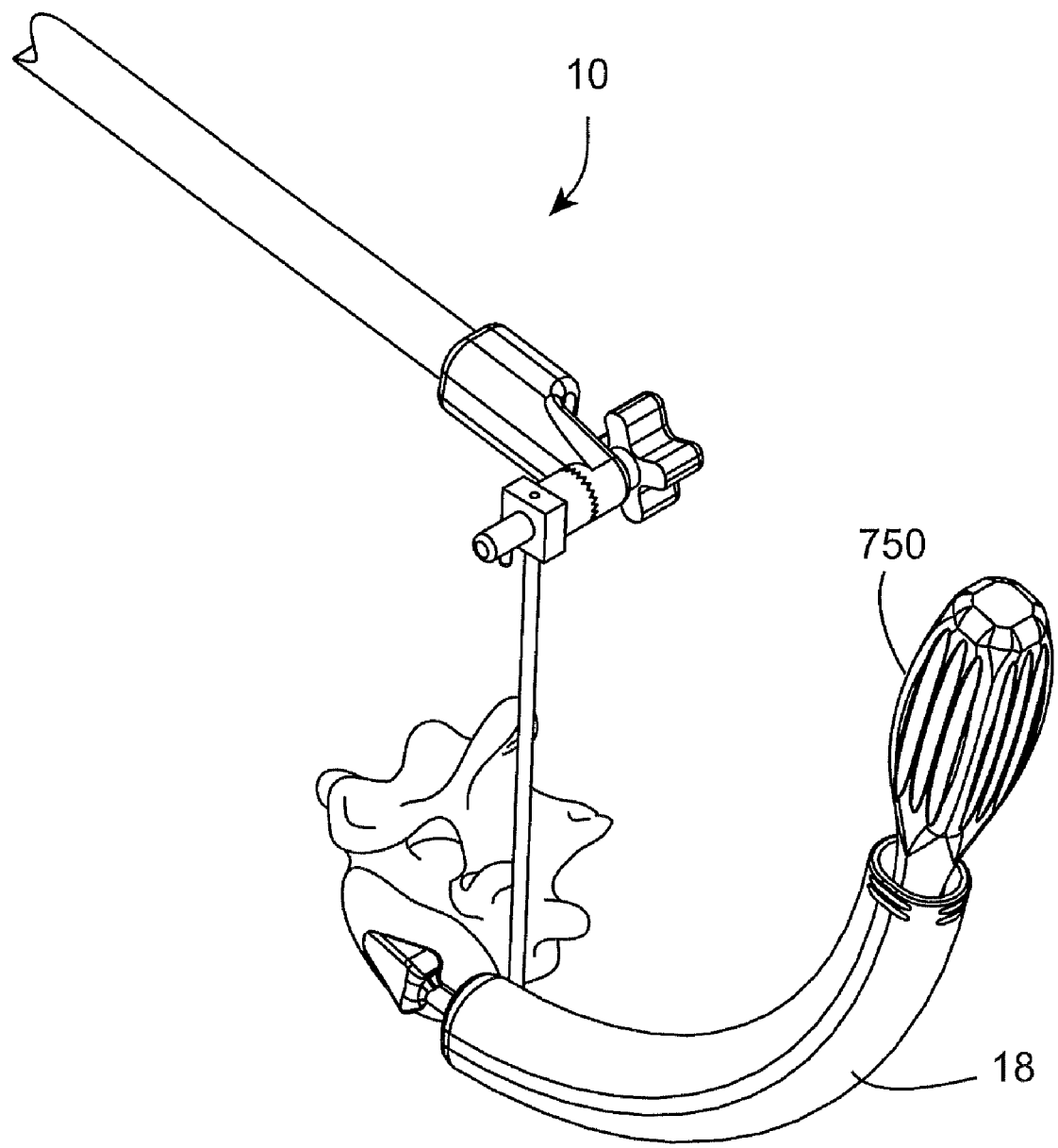
FIG. 17 is a perspective view of an arcuate cannula assembly with a curved wedge distracter instrument inserted into a cannula, adjacent a portion of the spine.

In FIG. 17, an instrument with a curved shaft is inserted through the arcuate cannula 18 of the arcuate cannula assembly 10 to reach the location of a spinal procedure. One vertebra is shown to provide perspective; a second is omitted so that a working end of the instrument may be seen. Wedge distractor 750, with a wedge head, is inserted through cannula 18 to reach the intervertebral space. A working portion of the wedge distractor 750 includes a working end, in this case the wedge head, and a shaft that couples the working head to a handle. The arcuate shaft may be curved, and may indeed be curved along a constant radius to provide an arcuate shaft that passes through the arcuate envelope defined by the interior surface of the arcuate cannula 18.

One of skill in the art will recognize that many different spinal surgery tools may be adapted for use through cannula 18. These tools will tend to have a handle, a curved or a flexible shaft and a working end. Examples are present in co-pending U.S. patent application Ser. No. 12/357,596, filed Jan. 22, 2009, for SPINAL ACCESS SYSTEM AND METHODS which was referenced above and incorporated by reference. Interested readers may review details of various tools within that application.

Instruments formed with flexible shafts may also be used to reach through cannulas which are curved, but do not have a fixed radius of curvature.

To perform a particular spinal procedure, one or more of the curved instruments set forth above may be inserted through the arcuate cannula to access the spinal surgical site. For example, to perform an interbody device implantation between two vertebrae, one or more instruments may be employed to prepare the intervertebral space and vertebral endplates. The first instrument is removed and a second preparatory instrument, or more, from the same group may be inserted and used if necessary. When preparation of the intervertebral space and endplates is complete, a curved trial implant instrument (not shown) may be used to insert variously sized trial implants through the cannula to determine the correct size for an interbody implant. Finally, the interbody implant 300 (FIG. 15B) is inserted through the cannula using a curved implant inserter, released and implanted in the interbody space. A curved tamp may then be used to adjust the positioning of the implanted implant 300.

Figure 18:
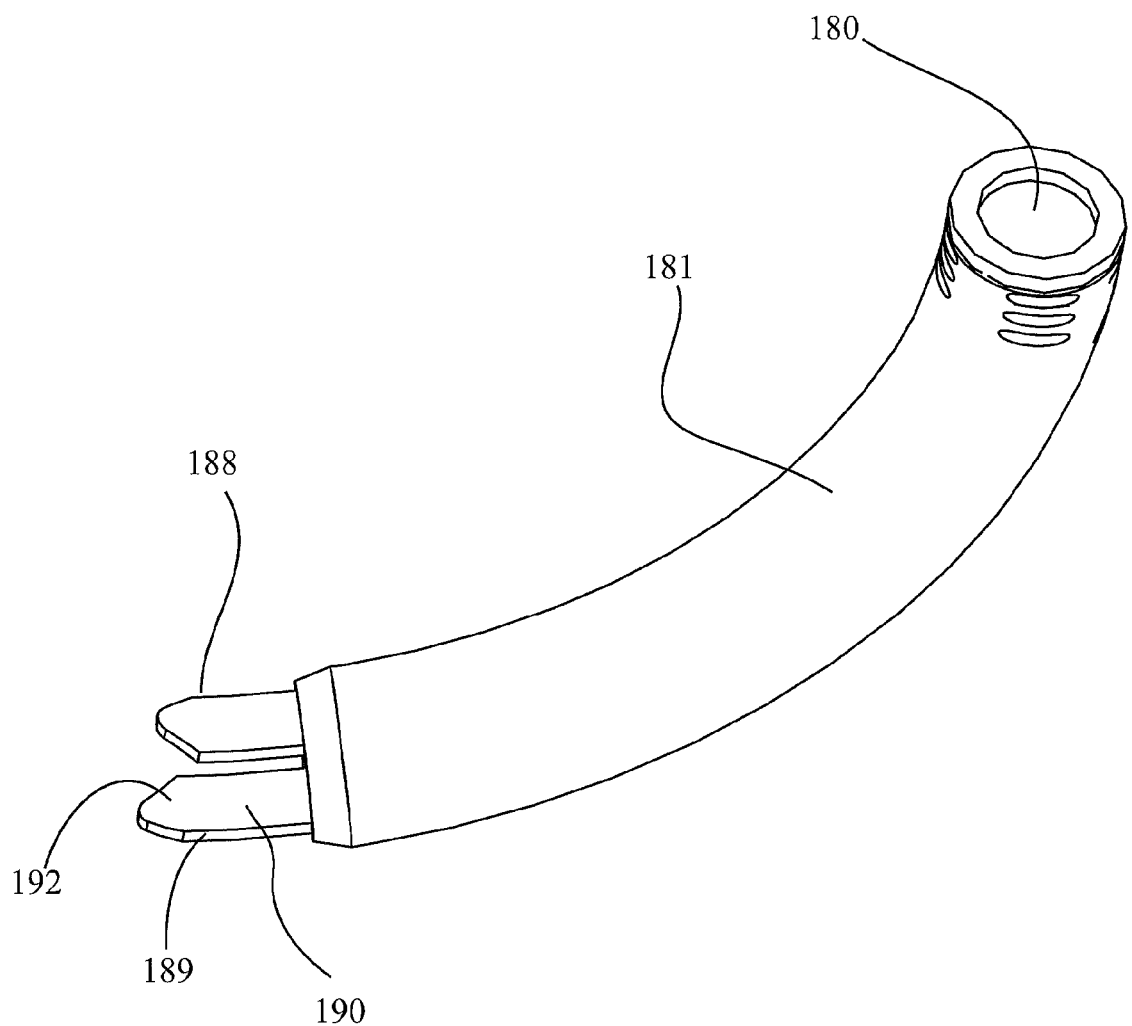
FIG. 18 is a perspective posterior view of a curved cannula with tang extensions inside a larger curved cannula.
Figure 19:
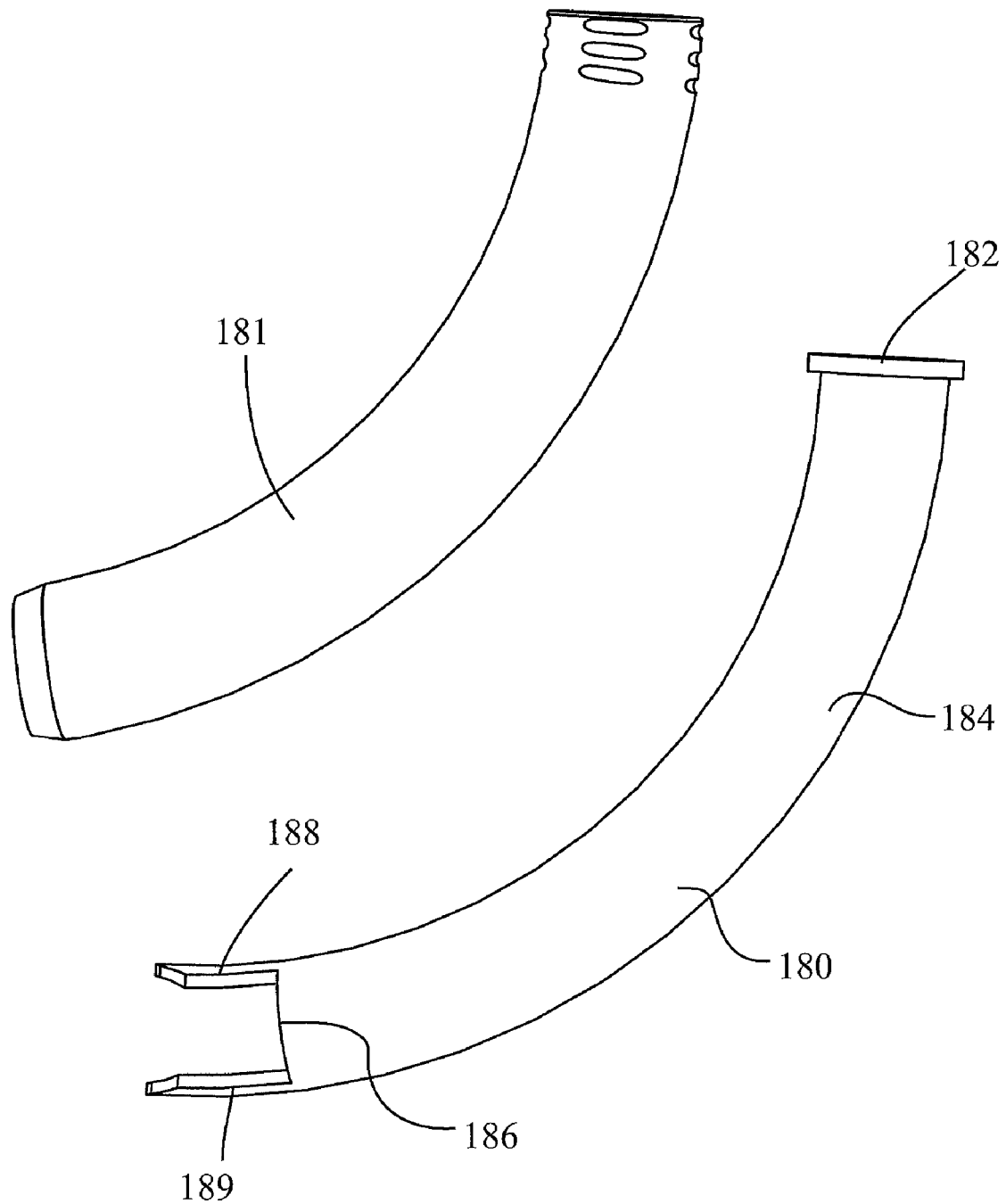
FIG. 19 is a posterior view of the cannulas of FIG. 18 placed side by side.

Referring to FIG. 18 and FIG. 19, a tanged cannula insert 180 that has two pronged extensions is shown inside a slightly larger diameter cannula 181. Cannula insert 180 includes a proximal end 182, a curved shaft 184, and a distal end 186. Extending distally from the distal end 186 are two tangs 188, 189. The tangs each may have a curved body 190 with a tapered end 192. In an alternative embodiment, at least one of the tangs may comprise at least one flat portion. The tangs 188, 189 may be inserted through the cannula 181 into the intervertebral space between two adjacent vertebrae to securely dock the cannulas 180, 181 adjacent the intervertebral space, providing access for a surgical procedure to be performed within the intervertebral disc space.

The tangs 188, 189 may be located as illustrated in FIG. 18, so that upon insertion each tang spans a portion of the intervertebral space and has an edge oriented toward each vertebral body. In alternative embodiments, the tangs may be located such that each tang is facing one vertebral body upon insertion. The tapered ends 192 may allow the tangs 188, 189 to penetrate the disk annulus, if present. Insertion of the tanged cannula 180 through cannula 181 allows the tangs 188, 189 to reach the intervertebral space without catching on or otherwise encountering or damaging body tissues between the insertion point and the intervertebral space.

Proximal end 182 may comprise a rim, lip or other feature which engages with the larger cannula 181 to limit how far the tanged cannula insert 180 may be inserted into the intervertebral space. The tanged cannula insert and other cannulas described herein may be arcuate, with a fixed radius of curvature. Tanged cannula insert 180 may be configured to be insertable into other cannulas described herein, such as cannula 18. Tanged cannulas with graduated sizes of tangs may be sequentially deployed.

The purpose of the tanged cannula insert may be four-fold: 1) docking the cannulas to the disc space, to ensure little to no movement of the cannulas throughout the surgical procedure; 2) maintaining the height of the disc space during subsequent procedures such as interbody implantation; 3) providing a working channel for the surgical procedures to be performed, and 4) protecting anterior and/or posterior vessels or structures as instruments are inserted into the intervertebral space, by blocking access to the vessels.

Figure 20:
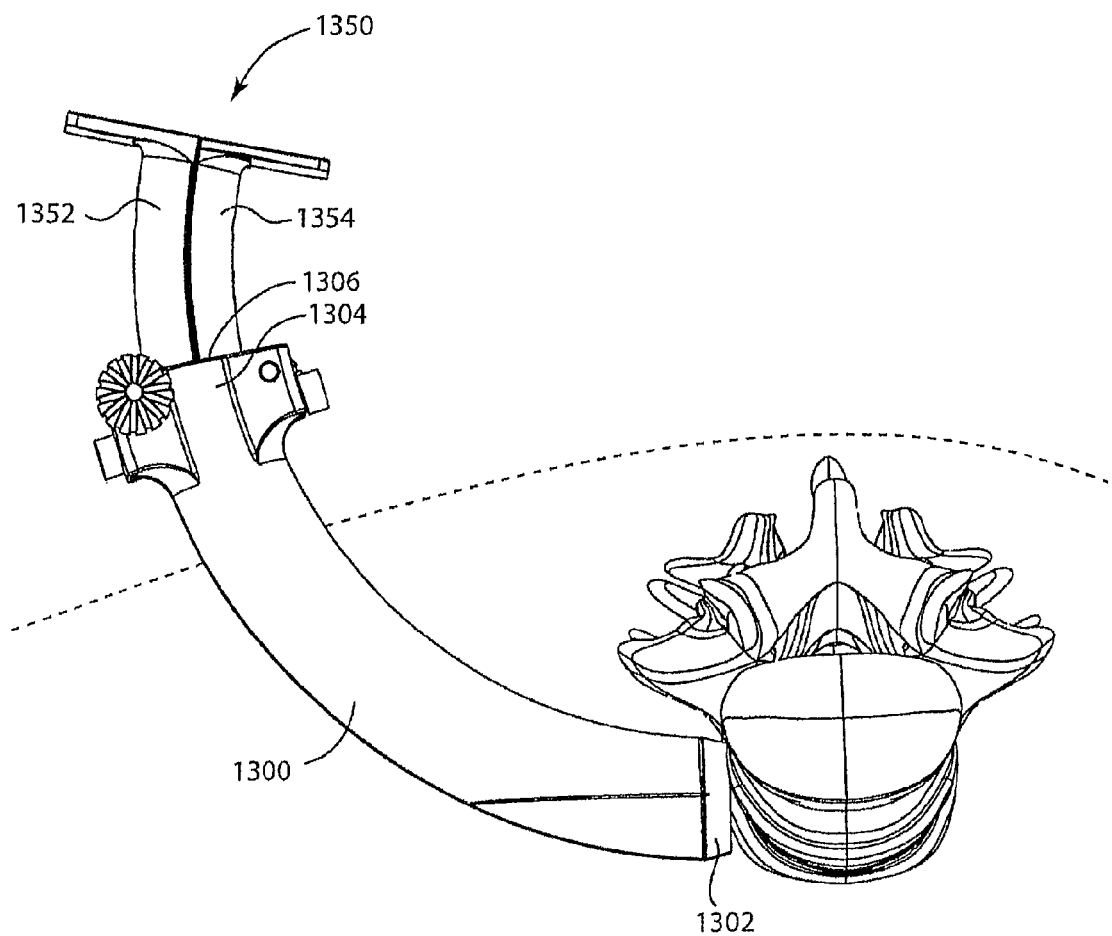
FIG. 20 is a cephalad view of a curved cannula adjacent a portion of a spine, with a two-piece tang assembly partially inserted into the cannula.

Referring to FIG. 20, a system for providing surgical access to a portion of a spine is shown from a caudal perspective. An arcuate cannula 1300 is configured to be inserted into the spinal area from a latero-posterior approach. Arcuate cannula 1300 may comprise aluminum or another biocompatible radiolucent material. To one of skill in the art, radiolucent conveys—not radio-opaque. Radiolucent may be almost entirely transparent to x-ray photographs and fluoroscopy but frequently an item that is radiolucent is not entirely transparent in a fluoroscopic image.

For the purposes of this disclosure, radio-opaque does not need to be one hundred percent opaque. Markers will be effective as long as the image of the marker is sufficiently distinctive to be used as an effective marker within fluoroscopic imaging.

A distal end 1302 of the cannula 1300 is positioned adjacent the spine, and may be more specifically positioned tangential to an interspinous space, to provide access to the interspinous space for surgical procedures such as discectomy and/or disc replacement, among others. A proximal end 1304 of the cannula provides an opening 1306 for insertion and manipulation of tools and instruments for surgical techniques and for visualization and targeting of surgical procedures. A tang assembly 1350 is shown partially inserted into the arcuate cannula 1300, the tang assembly 1350 comprising an anterior tang portion 1352 and a posterior tang portion 1354.

Figure 21:
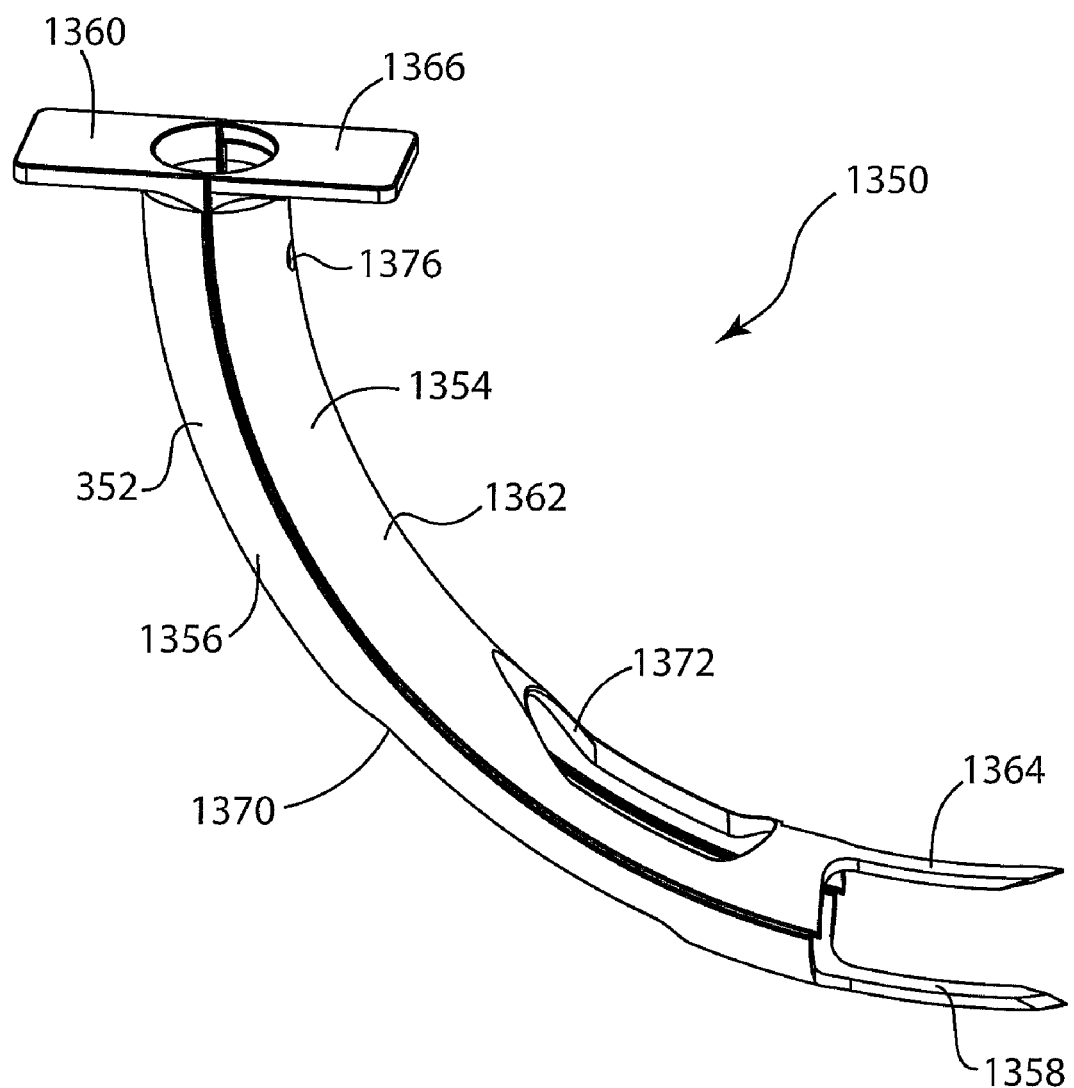
FIG. 21 is a perspective view of the two-piece tang assembly of FIG. 20.
Figure 22:
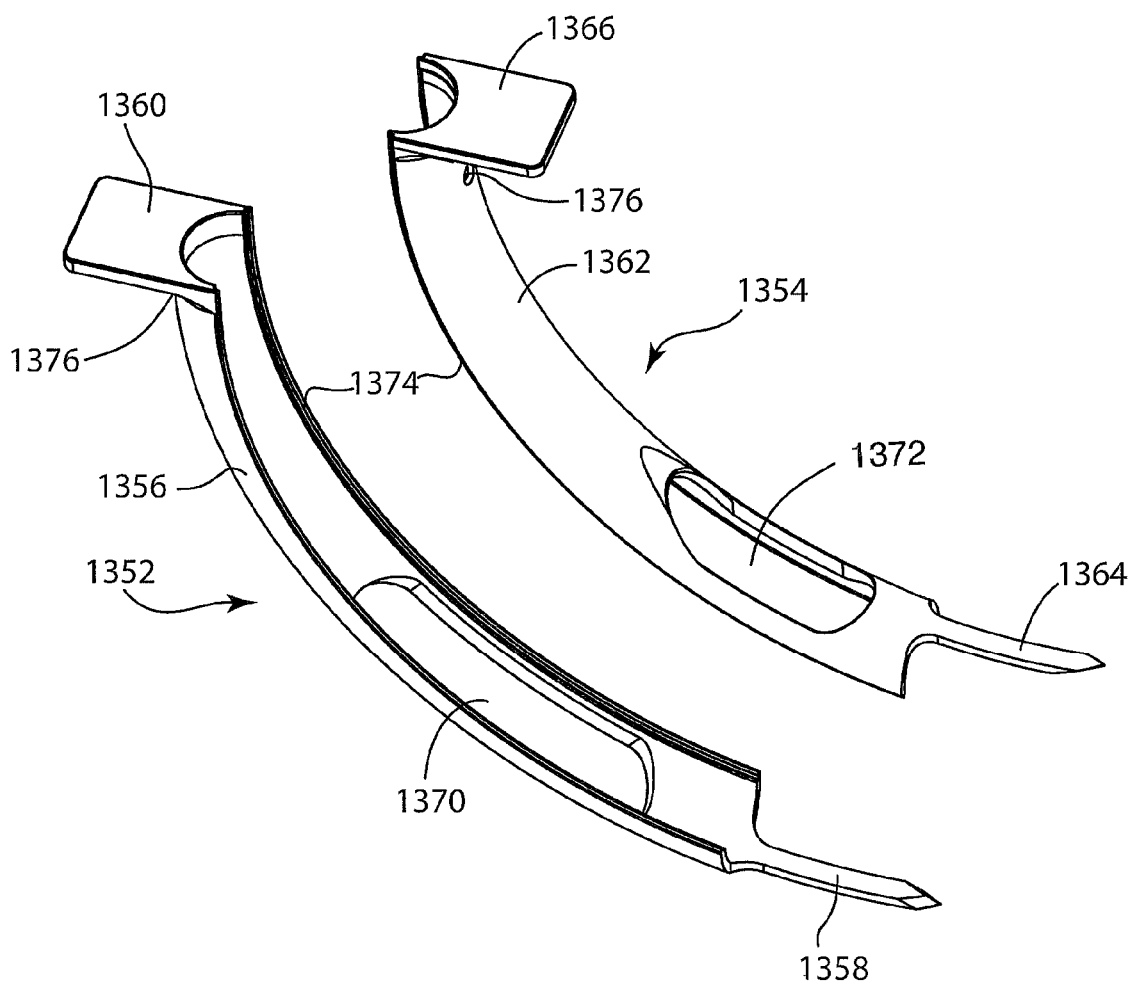
FIG. 22 is an exploded perspective view of the two-piece tang assembly of FIG. 20.

Referring to FIG. 21 and FIG. 22, the tang assembly 1350 is shown in greater detail. Anterior 1352 and posterior 1354 tang portions are shaped to fit together to form a cannula which is sized to be inserted into the arcuate cannula 1300 (FIG. 20). Anterior tang portion 1352 includes a curved anterior body portion 1356, a distal end with an anterior tang extension 1358, and a proximal end with an anterior handle 1360. The anterior handle 1360 may be formed monolithically with the body portion 1356, or may be separately formed. The anterior tang extension 1358 is generally narrow, pointed and shaped to fit into the interspinous space between two vertebral bodies, where it may retract tissues, allowing access to the interspinous space.

The posterior tang portion 1354 is shaped to complement the anterior tang portion 1352, such that together they form an arcuate cannula. The posterior tang portion 1354 includes a curved posterior body portion 1362, a distal end with a posterior tang extension 1364, and a proximal end with a posterior handle 1366.

The anterior body portion 1356 may have an anterior window 1370, and the posterior body portion 1362 may have a posterior window 1372. The windows 1370, 1372 may allow for visualization and targeting of surgical procedures, using radiography, or other techniques. Tang assembly 1350 may comprise stainless steel or another biocompatible material. Stainless steel or a material of similar strength may be preferred to provide sufficient rigidity to the narrow tang extensions 1358, 1364 to prevent bending or other distortion during insertion and other procedures. Through use of the windows 1370 and 1372, the tang assembly may use materials that are radio-opaque while retaining the option to look at radio-opaque markers on the arcuate cannula 1300 as discussed below. One of skill in the art will recognize that the windows could be made of radiolucent material or could be radiolucent through simply having an opening framed by the window to allow fluoroscopic imaging to be unimpeded as it passes through the windows 1370 and 1372.

It is appreciated that alternative embodiments of the tang assembly may include tang extensions located at different angles, to allow insertion along different planes. Specifically, the tang extensions may be located at a 45 degree angle relative to the handles.

Each tang portion 1352, 1354 may have guiding features 1374 such as rims, ridges or slots, or a combination thereof, on their longitudinal edges. These guiding features 1374 may allow the tang portions 1352 and 1354 to slide into alignment and join with one another as they are inserted, and may prevent misalignment or separation after the two portions are joined together. Each tang portion 1352, 1354 may also have a locking feature such as a locking port 1376.

Figure 23:
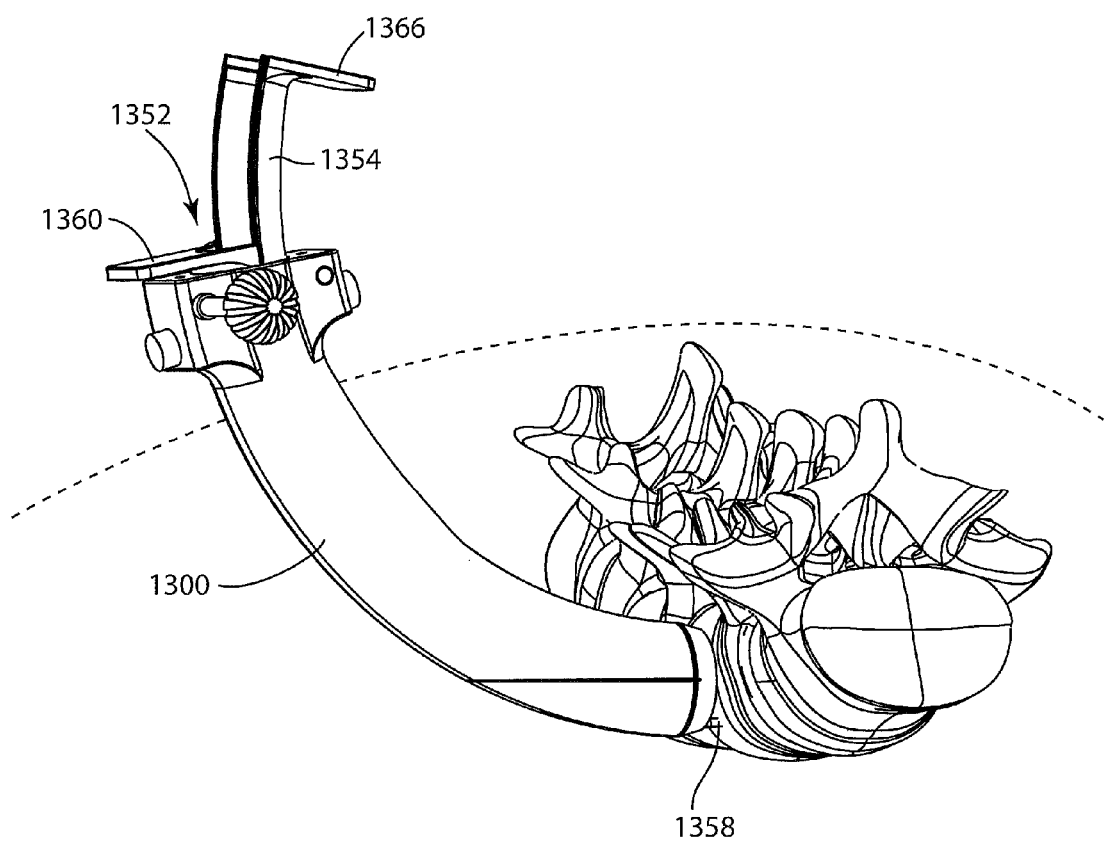
FIG. 23 is a medial-cephalad view of the cannula, two-piece tang assembly and spine of FIG. 20, with one tang piece partially inserted into the cannula.
Figure 24:
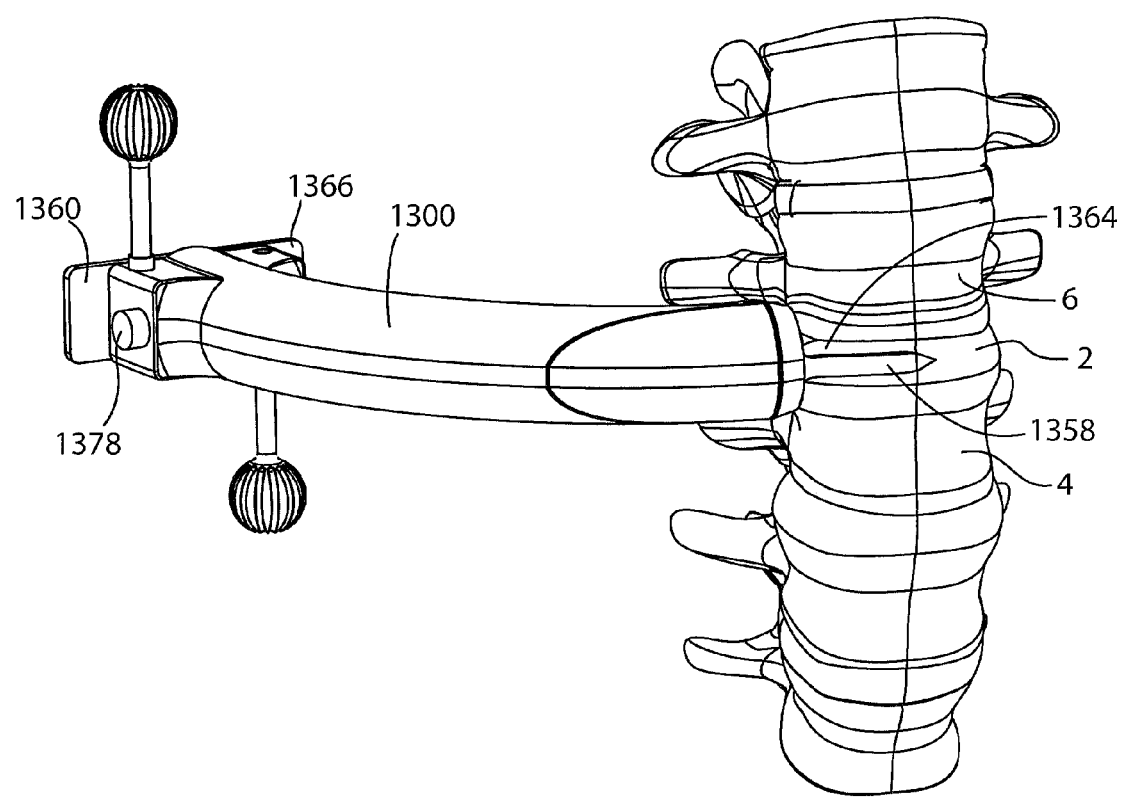
FIG. 24 is an anterior view of the cannula, two-piece tang assembly and spine of FIG. 20.

FIG. 20, FIG. 23 and FIG. 24 illustrate how the tang assembly 1350 may be inserted into the arcuate cannula 1300. FIG. 20 shows anterior 1352 and posterior 1354 tang portions being inserted into the cannula 1300 substantially simultaneously. The guiding features 1374 on each longitudinal edge may have been joined prior to insertion into the cannula. Insertion may continue until the tang extensions are positioned in the interspinous space, and the handles 1360, 1366 are adjacent the proximal end 1304 of the cannula, preventing further insertion.

FIG. 23 illustrates separate insertion of the tang portions 1352, 1354 into the cannula 1300. Anterior tang portion 1352 has been fully inserted, and posterior tang portion 1354 has been partially inserted. The tang portions may be inserted in either order, or together as previously described. During a procedure, a practitioner may also choose to only insert one tang portion, anterior or posterior, if desired.

FIG. 24 is an anterior perspective view illustrating tang portions 1352, 1354 (with only the two handles visible 1360 and 1366) fully inserted into the arcuate cannula 1300. Locking features such as locking ports 1376 (FIG. 22) may cooperate with locking members 1378 to form locking mechanisms which can lock each tang portion in place in the cannula 1300, preventing movement including back-out from the arcuate cannula 1300.

Locking member 1378 may comprise a bolt, pin, spring pin, snap, or other member capable of forming a locking mechanism with tang portion 1352 and/or 1354.

Anterior tang extension 1358 extends generally medial-laterally across the anterior edge of intervertebral space 2 between vertebral bodies 4 and 6. Opposite from anterior tang extension 1358, posterior tang extension 1364 extends generally medial-laterally across the posterior edge of intervertebral space 2 between vertebral bodies 4 and 6. The tang extensions 1358, 1364 may maintain the vertebral body spacing and provide tissue retraction, preventing unwanted tissue encroachment into the intervertebral space 2 during subsequent surgical procedures. Upon completion of the surgical procedures, the tang portions 1352, 1354 may be unlocked and removed from the cannula 1300, either singly or together.

Figure 25:
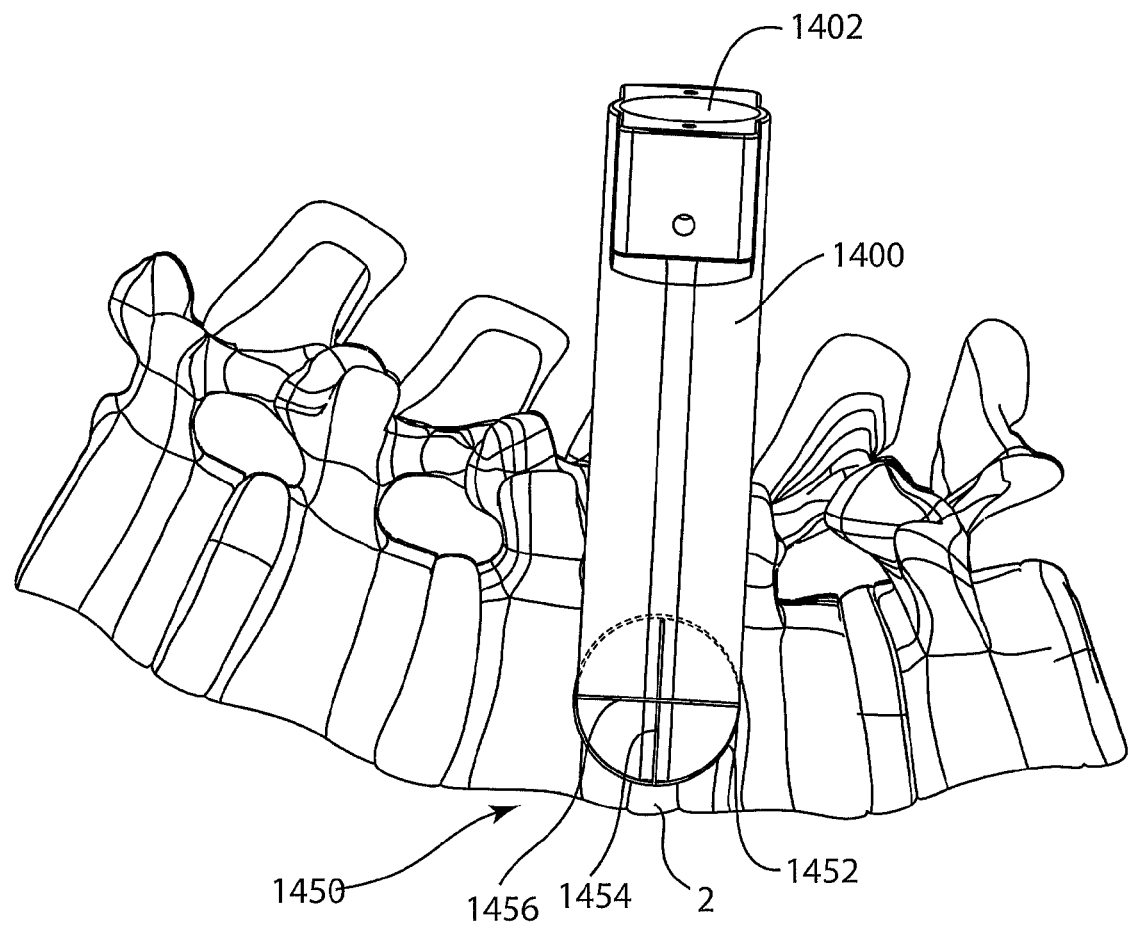
FIG. 25 is a medial view of an arcuate cannula with a referencing marker system, adjacent a portion of a spine.
Figure 26:
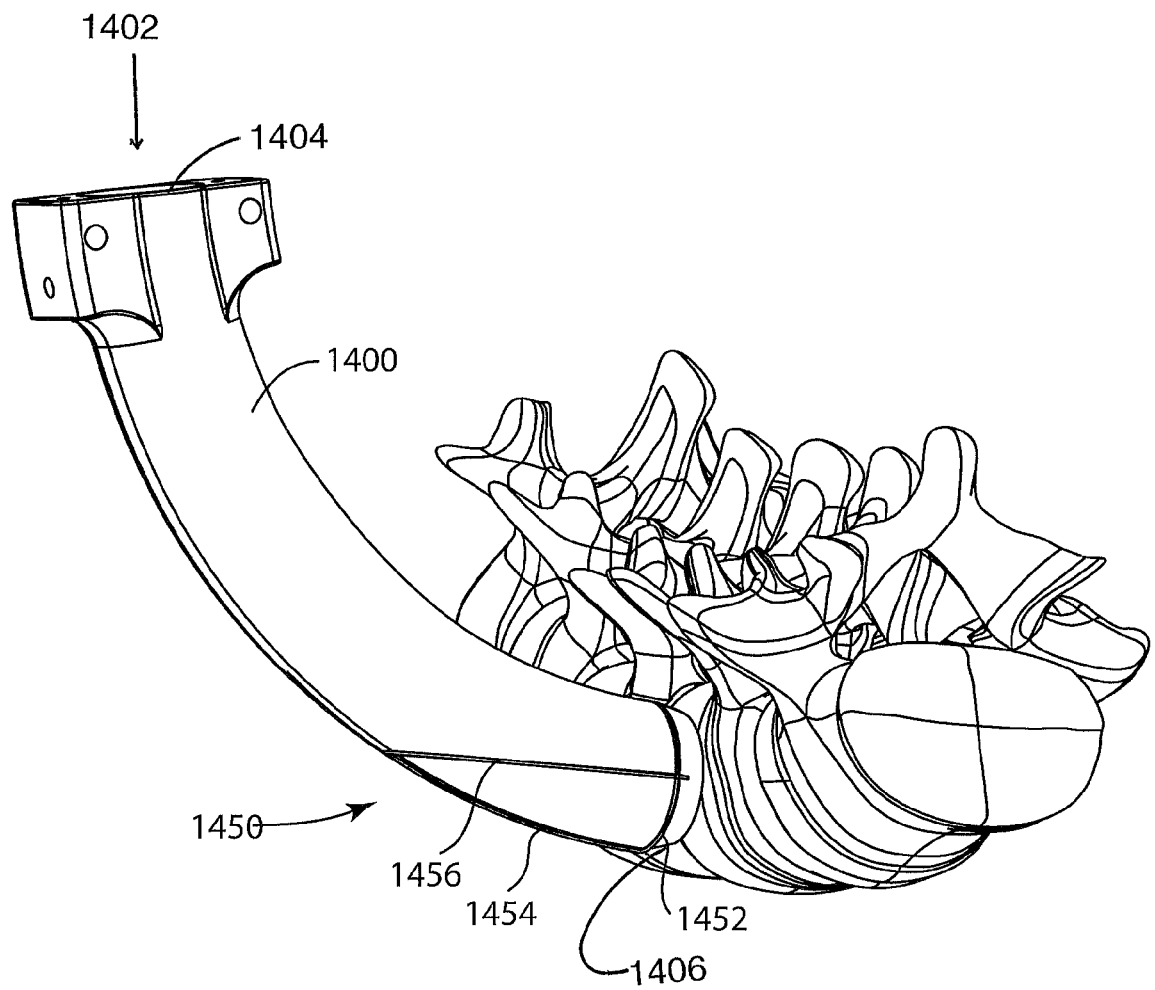
FIG. 26 is a medial-cephalad view of the cannula, referencing marker system and spine of FIG. 25.
Figure 27:
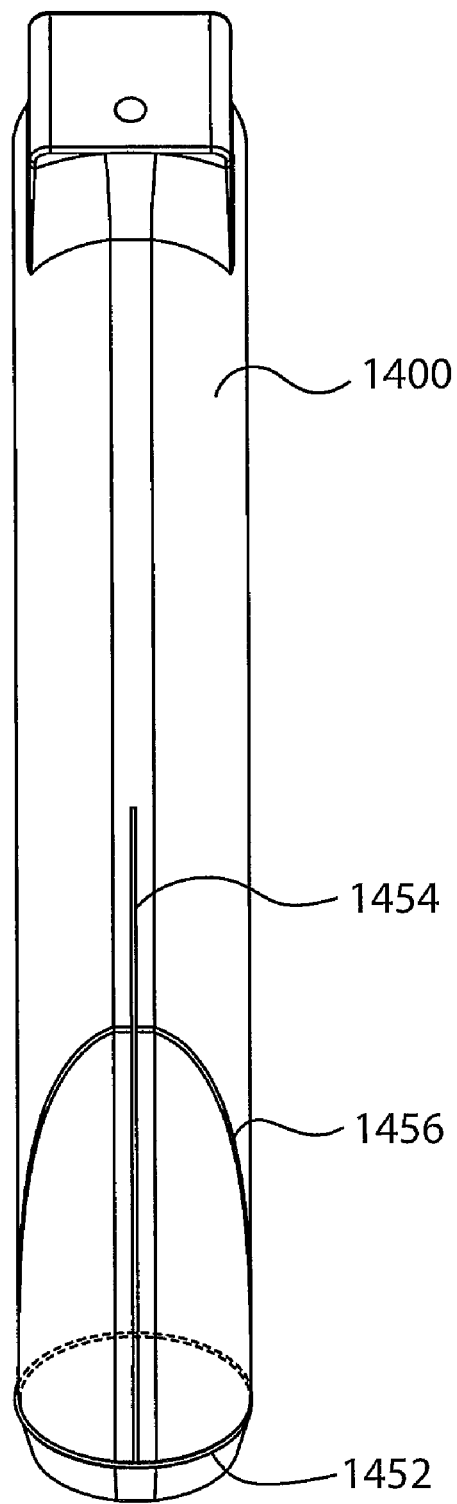
FIG. 27 is a perspective view of the cannula and referencing marker system of FIG. 25.

FIG. 25, FIG. 26, and FIG. 27 illustrate an embodiment of a visual referencing system for use with a spinal access cannula.

Referring to FIG. 25, a lateral view of a portion of a spine is shown, with arcuate cannula 1400 positioned to extend from a latero-posterior location to an interspinous space 2.

FIG. 26 illustrates the cannula 1400 and the marker system 1450 from a caudal perspective. The central bore 1402 runs from the proximal opening 1404 to the distal opening 1406.

FIG. 27 illustrates the cannula 1400 and components of one implementation of a marker system 1452, 1454, and 1456 from a latero-anterior perspective. The cannula 1400 may comprise aluminum or another radiolucent material.

Continuing to reference FIG. 25, FIG. 26 and FIG. 27, the cannula 1400 further includes a visual referencing, or marker system 1450, which in turn includes radio-opaque markers joined to the cannula 1400. The markers may comprise strips of tantalum (Ta) or other radio-opaque material, and may be joined to the cannula through operations including laser welding, brazing, tape, adhesive, paint, or heat bonding, among other methods. A first marker 1452 encircles a perimeter of the cannula 1400 in the vicinity of circular distal opening 1406 of the cannula 1400.

The phrase in the vicinity of includes near and at. Thus, first marker 1452 may encircle a perimeter near the distal opening 1406 or may actually encircle the distal opening 1406.

A second marker 1454 extends from in the vicinity of the distal opening 1406 of the cannula 1400 along the cannula's anterior wall a portion of the distance towards the proximal opening 1404.

A third marker 1456 arcs from a lateral side of the cannula in the vicinity of the distal opening 1406 across the second marker 1454 and to the opposite side of the cannula 1400 in the vicinity of the distal opening 1406.

When the arcuate cannula 1400 is in a preferred orientation, and radiographically viewed from a lateral perspective, the three markers 1452, 1454, and 1456 combine to form a cross hair in a circle, as seen in FIG. 25. A combination of antero-posterior and lateral radiographs may be used as guides to align the markers. In a preferred orientation in which the distal opening of the arcuate cannula 1400 is tangential to the interspinous space 2 (FIG. 25), the cross hairs are aligned or targeted on the interspinous space.

Third marker 1456, which has a general orientation in the cephalad-to-caudal direction when the cannula 1400 is positioned relative to the spine as shown in FIG. 26, forms an upwards facing arc when the distal end 1402 of the arcuate cannula 1400 is pointing more posterior and forms a downward facing arc when the distal end is facing more anterior. This helps to guide the surgeon such that the exit direction of the instruments and implants that are delivered through the cannula 1400 eventually exit in a preferred orientation. This preferred orientation prevents the instruments and implants delivered through the cannula 1400 from exiting the disc space and disrupting the anterior vascular structures or the posterior neurovascular tissues. Once a preferred orientation is achieved, the cannula 1400 may be locked into that orientation via an external clamping system or other locking device.

The arcuate cannula 1400 and marker system 1450 may be used in conjunction with the tang assembly 1350 discussed above. The anterior 1352 and posterior 1354 tang portions may be inserted through the cannula 1400, with the tang extensions 1358, 1364 bracketing the interspinous space. The windows 1370, 1372 are positioned to cooperate with the markers 1452, 1454, and 1456 to allow visualization of the markers during radiography.

FIG. 28A shows a lateral view of a spine with vertebrae 4 and 6 and intervertebral disc space 2. Markers 1452, 1454, and 1456 create a marker image indicative of a cannula with the distal opening pointed posteriorly rather than laterally. To highlight the impact of the marker image, the radiolucent cannula is excluded from FIG. 28A but shown in FIG. 28B. FIG. 28B shows the corresponding cannula 1400 improperly directed posteriorly rather than laterally along with markers 1452, 1454, and 1456.

FIG. 29A shows a lateral view of a spine with vertebrae 4 and 6 and intervertebral disc space 2. Markers 1452, 1454, and 1456 create a marker image indicative of a cannula rotated from disc transverse midline. To highlight the impact of the marker image, the radiolucent cannula is excluded from FIG. 29A but shown in FIG. 29B. FIG. 29B shows the corresponding cannula 1400 from an anterior/posterior view along with the positions of the markers 1452, 1454, and 1456.

Figure 30B:
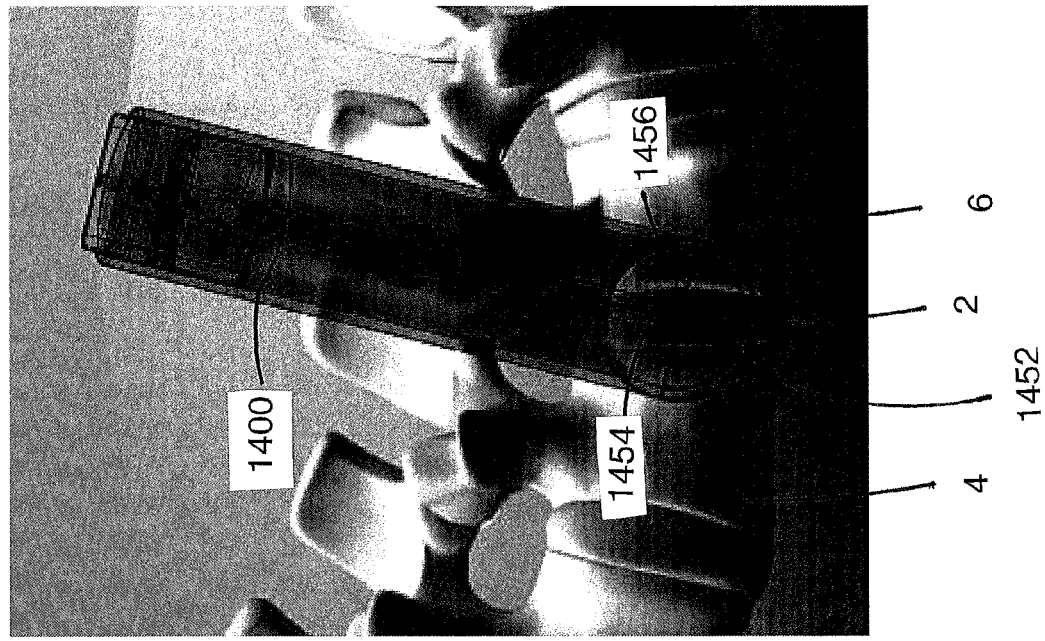
FIG. 30A and FIG. 30B show a marker image corresponding to a cannula positioned out of alignment with the vertebrae endplates.
Figure 30A:
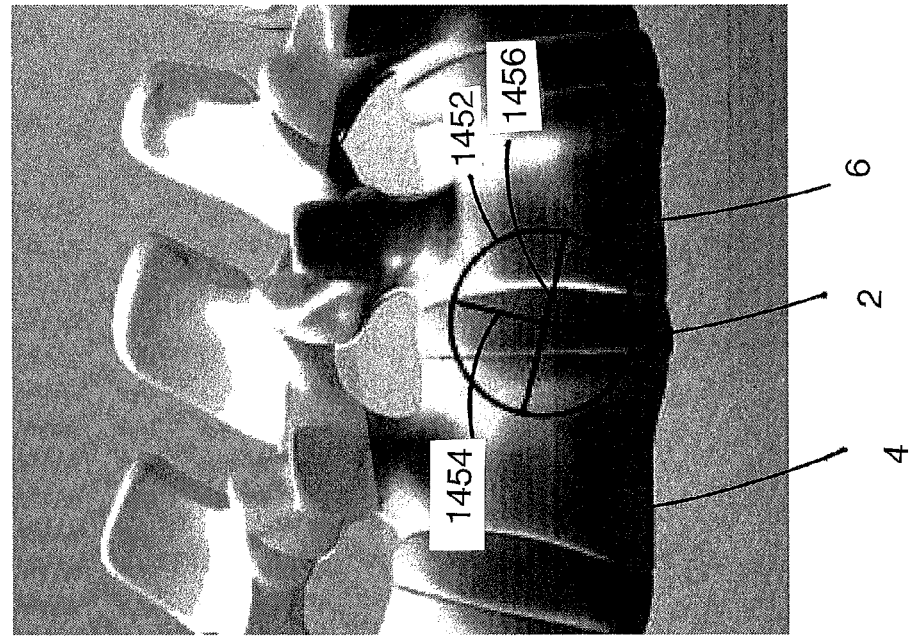

FIG. 30A shows a lateral view of a spine with vertebrae 4 and 6 and intervertebral disc space 2. Markers 1452, 1454, and 1456 create a marker image indicative of a cannula with rotated so the cross hair from marker 1454 is not parallel with the vertebrae endplates. Unless this is the planned approach, the tangs will not be placed appropriately into the intervertebral disc space 2. To highlight the impact of the marker image, the radiolucent cannula is excluded from FIG. 30A but shown in FIG. 30B. FIG. 30B shows corresponding cannula 1400 along with markers 1452, 1454, and 1456.

Referring to FIG. 25, the marker system 1450 allows visual referencing of instruments and procedures relative to the cannula 1400 and the interspinous space. Radio-opaque instruments may be inserted through a central bore 1402 of the cannula and manipulated to carry out procedures in the interspinous space. Using the marker system 1450, the relative positions of such instruments relative to the cross hair and anatomy visible in fluoroscopy can be monitored through radiography.

Figure 31:
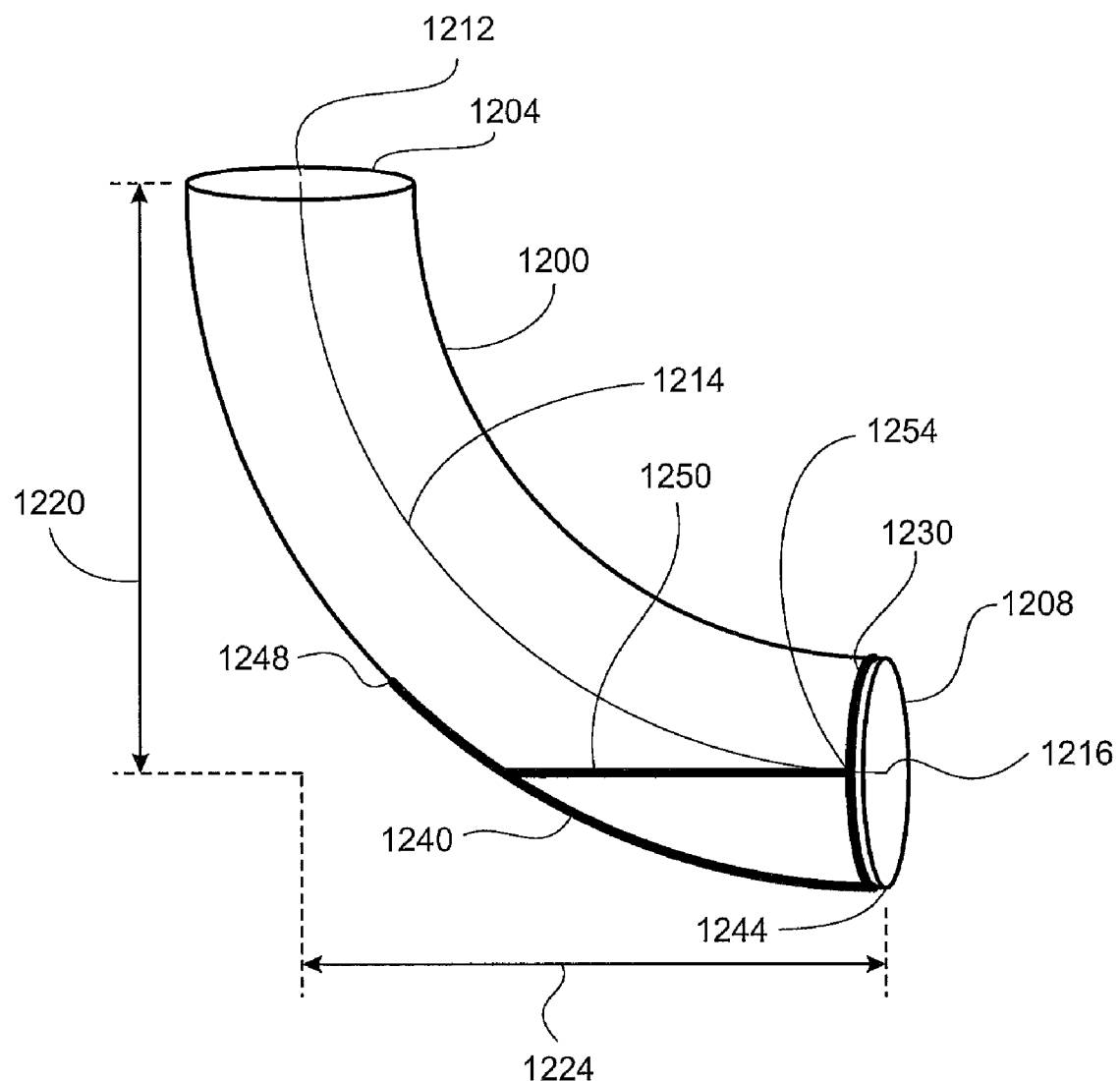
FIG. 31 shows a set of markers on a cannula 1200 relative to a depth axis and a lateral axis.

Referring to FIG. 31, a cannula 1200 is positioned relative to a pair of axes in order to discuss the markers without reference to the positioning of the patient as the cannula may be positioned in a variety of positions.

Cannula 1200 has a proximal opening 1204 and with a center point 1212 and a distal opening 1208 with a center point 1216. The two center points are connected by centerline 1214 that runs through the centerline of the cannula 1200. The center points 1212 and 1216 are separated by a distance along a depth axis 1220 and an offset along a lateral axis 1224 perpendicular to the depth axis 1220. While cannula 1200 shown here is an arcuate cannula that covers approximately 90 degrees so that the distal opening 1208 is substantially perpendicular to the proximal opening 1204, this is not a requirement for use of the teachings of the present disclosure. As discussed herein, other non-arcuate cannula or cannula of more than less than 90 degrees may be used to access a particular portion of the anatomy through an appropriate approach.

As discussed above, the cannula 1200 may have a set of at least one radio-opaque marker that will show up in fluoroscopy relative to the radiolucent cannula 1200 to provide an indication of the position of the distal opening 1208 relative to some other object or objects visible through fluoroscopy such as portions of the patient's anatomy, radio-opaque tool ends, or implants that are at least partially radio-opaque.

One marker may be a perimeter marker 1230 that marks a perimeter in the vicinity of the distal opening of the curved access cannula 1200. While the cross section of the cannula 1200 is a circle in this figure, as noted above, other cross sections may be used.

One marker may be a depth axis marker 1240 that runs along the cannula from the vicinity of the distal opening 1208 towards the proximal opening 1204 in a plane that contains the two center points oriented along the depth axis 1220 such that the depth axis marker provides a fluoroscopic image along the depth axis.

The cannula 1200 may include a marker 1250 that runs along the cannula 1200 at substantially a fixed depth value from the vicinity of the distal opening 1208 on one side to the vicinity of the distal opening on the other side. As noted above, "the vicinity" includes both near the distal opening and lines that end at the distal opening.

Marker 1250 provides a fluoroscopic image in the third plane that is perpendicular to the plane formed by the depth axis 1220 and the lateral axis 1224. Marker 1250 may be aligned with the center point 1216. One of skill in the art will recognize that one or more markers 1250 may be positioned at a depth that does not include the center point 1216 to form one or more marker images with constant depth values.

Alternatively, the curved cannula 1200 may be thought of in connection with three planes. A first plane containing the depth axis and the lateral axis and containing the center points 1212 and 1216. This plane may be called the longitudinal plane as it bisects the curved cannula along the curved length of the cannula. Marker 1240 is in the longitudinal plane.

A second plane of interest is a plane parallel to the distal opening 1208 and perpendicular to the longitudinal plane. This may be called the distal plane. Marker 1230 is in this distal plane.

A third plane of interest is perpendicular to both the longitudinal plane and the distal plane. The third plane includes center point 1216 but not center point 1212. Marker 1250 is in this third plane.

Many variations of marker images may be used within the scope of the teachings of the present disclosure including cross hair images that do not have a cross that touches the perimeter frame when the cannula is appropriately positioned. However, in order to achieve the particular cross hair image provided in the various drawings, the following relationships are relevant.

A) Marker 1240 in the longitudinal plane must extend up to a depth that matches the minimum depth of marker 1230 so that the top of the cross hair touches the circle.

B) Marker 1240 in the longitudinal plane must extend down to a depth that matches the maximum depth of marker 1230 so that the bottom of the cross hair touches the bottom of the circle.

C) Marker 1250 in the third plane extends to marker 1230 on both ends so that the horizontal line in the cross hair reaches to both sides of the circle.

The examples provided have used cross hairs that substantially aligned with the intervertebral disc space 2 such that one cross hair marker is substantially in the anterior-posterior direction and another cross hair marker is substantially aligned to the caudal-cephalad direction. If a curved cannula is used with an intended approach that is not aligned in the manner shown above, then the markers may be adjusted to provide a cannula that will provide substantially an anterior/posterior marker and a caudal/cephalad marker. In other words, placement of the markers may be shifted to allow for proper referencing to the spine from the intended approach.

Likewise, the tang portions and tang extensions could be adjusted to provide tangs that are substantially aligned with the intervertebral space when the cannula is positioned as intended for a given approach. Thus, a cannula and related components may be designed for a specific approach to the target area and a different cannula and related components used if a different approach is used.

Figure 32:
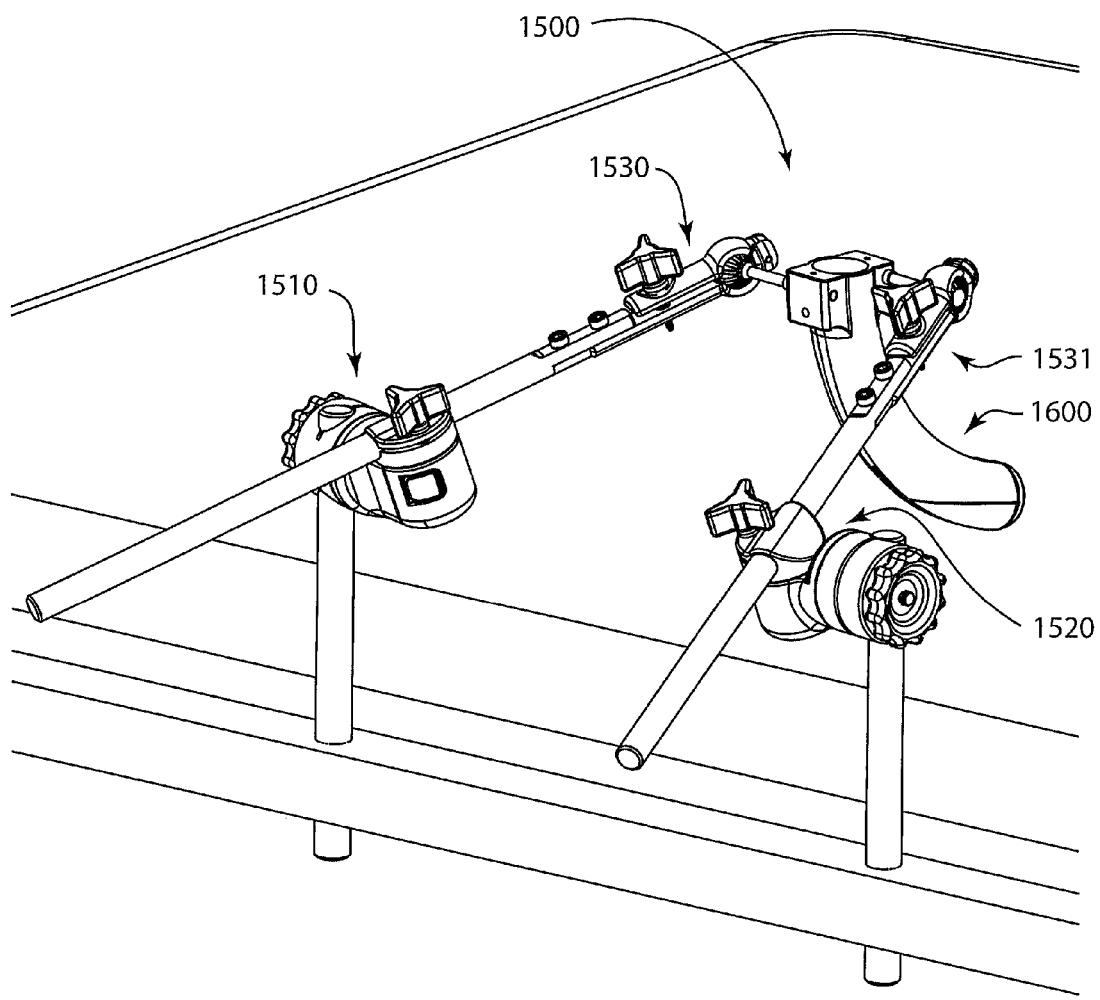
FIG. 32 is a perspective view of a positionable clamping system and the cannula of FIG. 20, attached to an operating table.

Referring to FIG. 32, a clamp system 1500 may be used to support, adjust, and lock the orientation and position of a spinal access cannula system 1600 relative to a patient and/or an operating table. Clamp system 1500 includes a first table mounted support system 1510, a second table mounted support system 1520, a first polyaxial clamp assembly 1530 and a second polyaxial clamp assembly 1531. First and second table mounted support systems 1510, 1520 may comprise identical components and may differ only in their relative orientation after assembly. Table mounted support systems 1510, 1520 are multi-axial and may be used to adjust the height of the spinal access cannula system 1600 relative to the table, the distance of the spinal access cannula system from the edge of the table, and the angular orientation of the spinal access system 1600 with respect to the table mounted support systems 1510, 1520.

First and second polyaxial clamp assemblies 1530, 1531 are identical and differ only in their positioning relative to the spinal access cannula system 1600.

Figure 33:
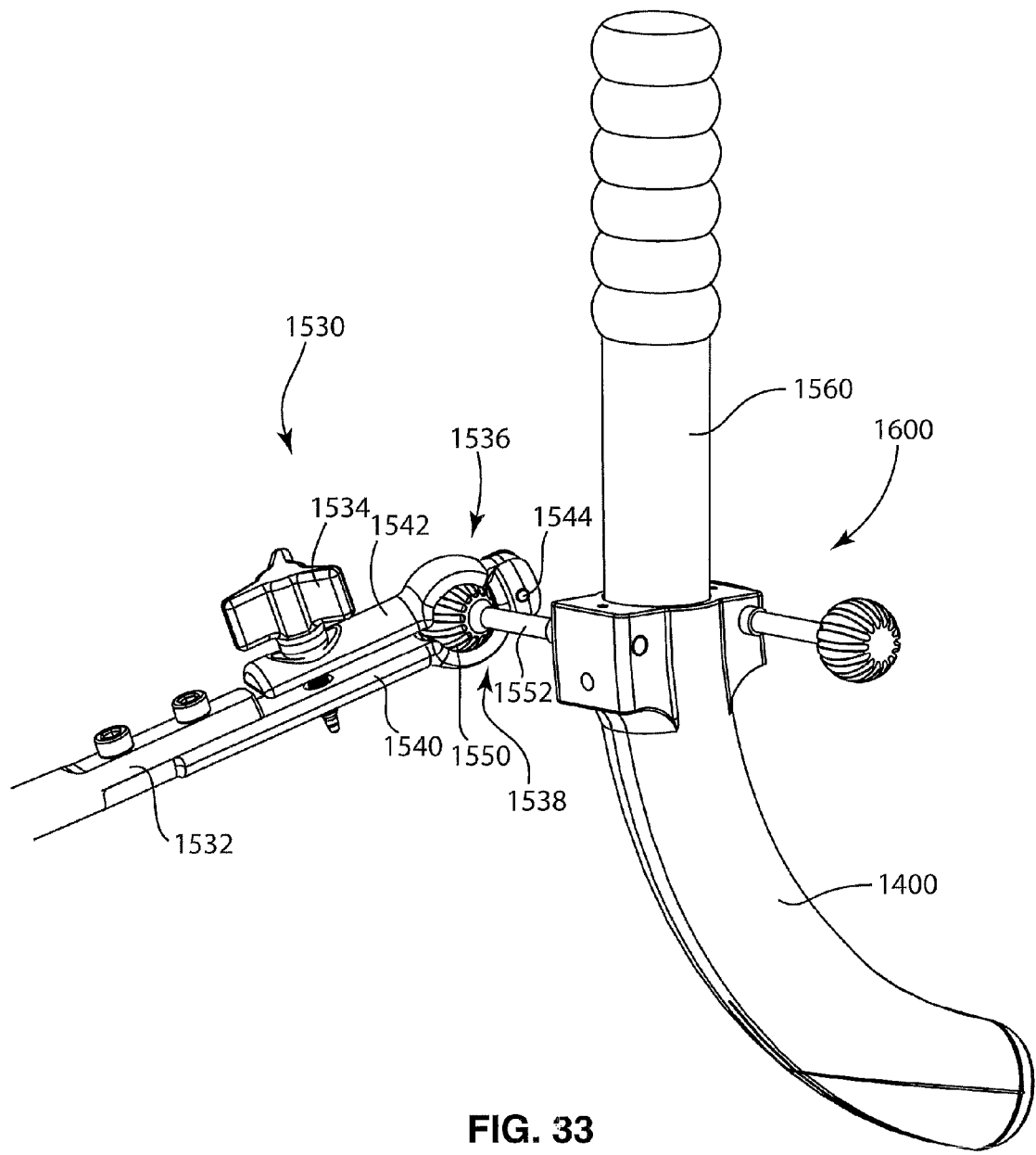
FIG. 33 is an enlarged view of a connection between the positionable clamping system and cannula of FIG. 32, and a joystick handle.
Figure 34:
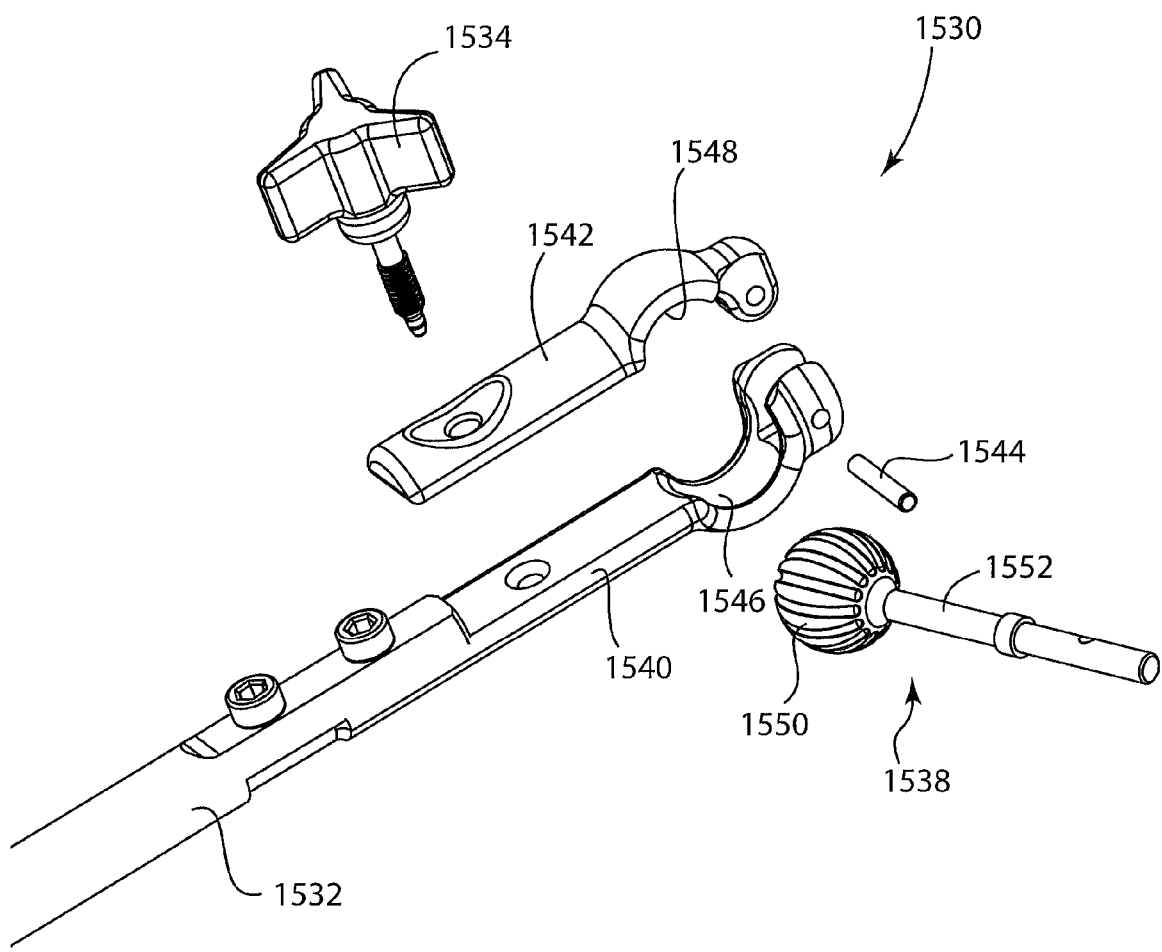
FIG. 34 is an exploded view of the connection of FIG. 33.

Polyaxial clamp assembly 1530 is shown in greater detail in FIG. 33 and FIG. 34. Polyaxial clamp assembly 1530 includes a support arm 1532, a fastener 1534, a clamp 1536, and a polyaxially adjustable linking member 1538. Support arm 1532 connects to the table mounted support system 1510 (FIG. 32), and is connected to the clamp 1536. Clamp 1536 includes a first jaw 1540, a second jaw 1542, and a hinge pin 1544. The support arm 1532 may be monolithically formed with the first or second jaw.

As best seen in FIG. 34, first jaw 1540 has a first spherical pocket 1546 and second jaw 1542 has a second spherical pocket 1548. The first and second jaws 1540, 1542 are joined by the hinge pin 1544 such that the first and second spherical pockets 1546, 1548 oppose one another.

Linking member 1538 includes a spherical head 1550 and a connecting rod 1552. Connecting rod 1552 may be rigidly connected to a spinal access cannula such as arcuate cannula 1400 (FIG. 33). Spherical head 1550 may be placed in the first spherical pocket 1546, and the second jaw 1542 closed such that the second spherical pocket 1548 surrounds the spherical head 1550. The polyaxial clamp assembly 1530 may be partially tightened by actuating the fastener 1534 to draw the first and second jaws together (1540 and 1542).

Before the polyaxial clamp assembly 1530 is fully tightened, the spherical head 1550 may be polyaxially rotated to provide a preferred orientation of the cannula 1400 (FIG. 33). Spherical head 1550 may be ridged, knurled, grooved or have other features or coatings to enhance a secure connection between the head and the jaws. When the preferred orientation is attained, the clamp 1536 (FIG. 33) is fully tightened by further actuation of the fastener 1534. A locking mechanism such as a nut (not shown) may lock the position of the fastener 1534.

Referring again to FIG. 33, optionally, a cannula extension 1560 may be inserted into the proximal end of the cannula 1400, and rotationally operated like a joystick to provide leverage to fine tune the orientation of the cannula 1400 before the clamp 1536 is fully tightened. If further adjustment is required, the clamp 1536 may be loosened by actuating the fastener 1534 and then re-tightened after polyaxial adjustment of the spherical head 1550. The fastener 1534 is offset from the first and second spherical pockets in the first and second jaws, which provides a mechanical advantage as the first and second jaws are drawn together to lock around the spherical head 1550.

Referring again to FIG. 32, the spinal access cannula system 1600 is held in place by first and second clamp assemblies 1530, 1531. These assemblies are joined to the cannula system 1600 on opposite sides of the cannula, such that each clamp/linking member connection is on a separate axis. This configuration prevents unwanted rotation of the cannula about either clamp/linking member axis. However, if desired only one side of the clamp system 1500 may be used, such as the first table mounted support system 1510, and the first polyaxial clamp assembly 1530, to provide unilateral support to the cannula system 1600. It is appreciated that clamp system 1500 may be configured to support arcuate cannula access system 10, 1600, or any targeting and/or access system disclosed herein.

Figure 35:
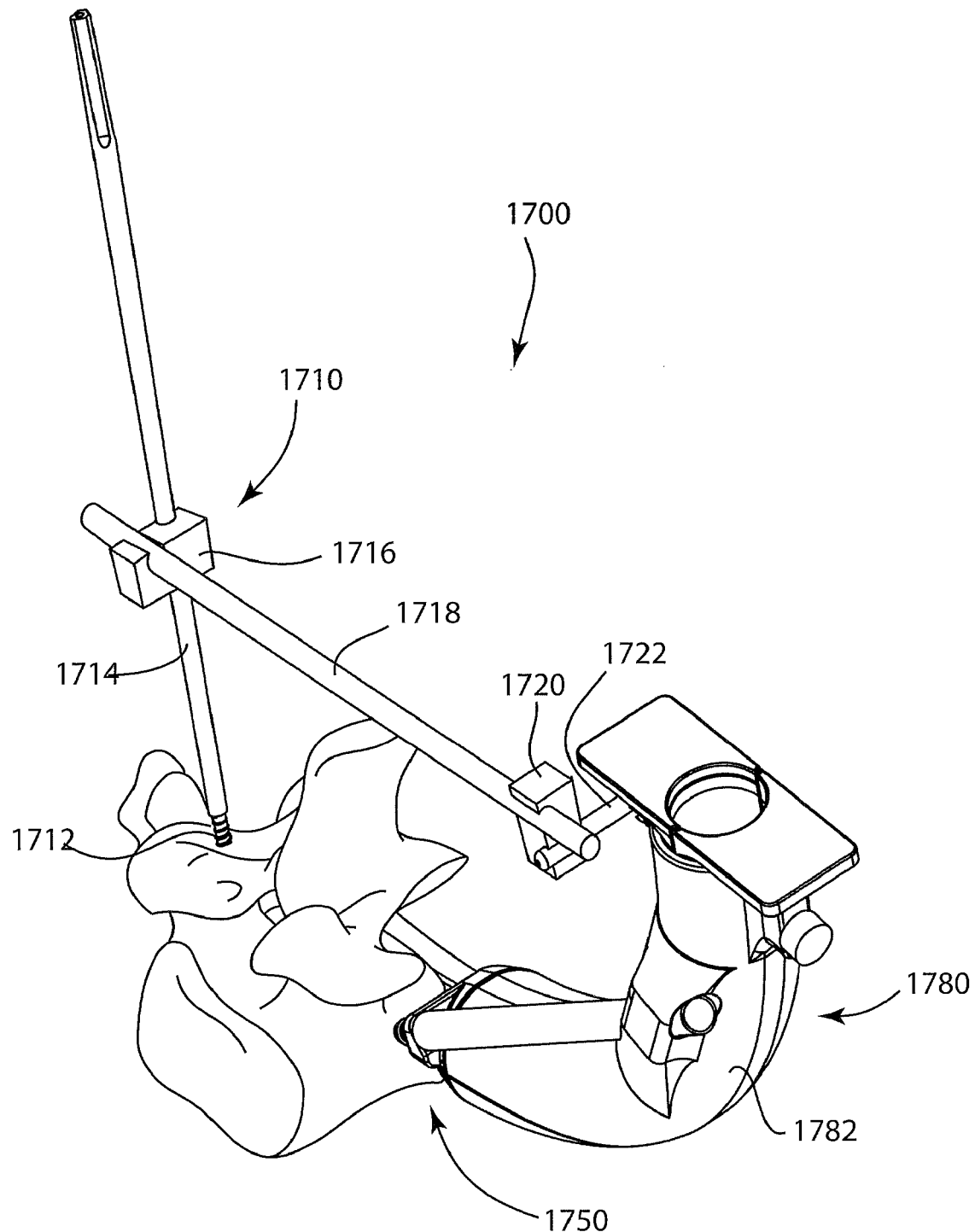
FIG. 35 is a posterior perspective view of an arcuate cannula, a tang assembly, a pedicle docking assembly and a vertebral body docking assembly, joined to a portion of a spine.

Referring to FIG. 35, an alternative embodiment of a spinal access cannula support system is shown. Vertebral docking system 1700 includes an adjustable pedicle docking assembly 1710, and a vertebral body docking assembly 1750, connected to a spinal access cannula assembly 1780. This system allows docking of the cannula assembly 1780 directly to the spine adjacent the spinal access cannula assembly 1780.

Pedicle docking assembly 1710 includes at least one pedicle screw 1712 joined to a first shaft 1714. A first clamping joint 1716 couples the first shaft 1714 to a second shaft 1718. Second clamping joint 1720 couples second shaft 1718 to a third shaft 1722, which is coupled to a proximal end of an access cannula 1782. Additional shafts and clamping joints may be added to the system as desired to add additional degrees of freedom of adjustability. Each clamping joint provides adjustability along at least two orthogonal axes. It is appreciated that polyaxial clamping joints could be provided which would provide additional adjustability along at least three axes.

Figure 36:
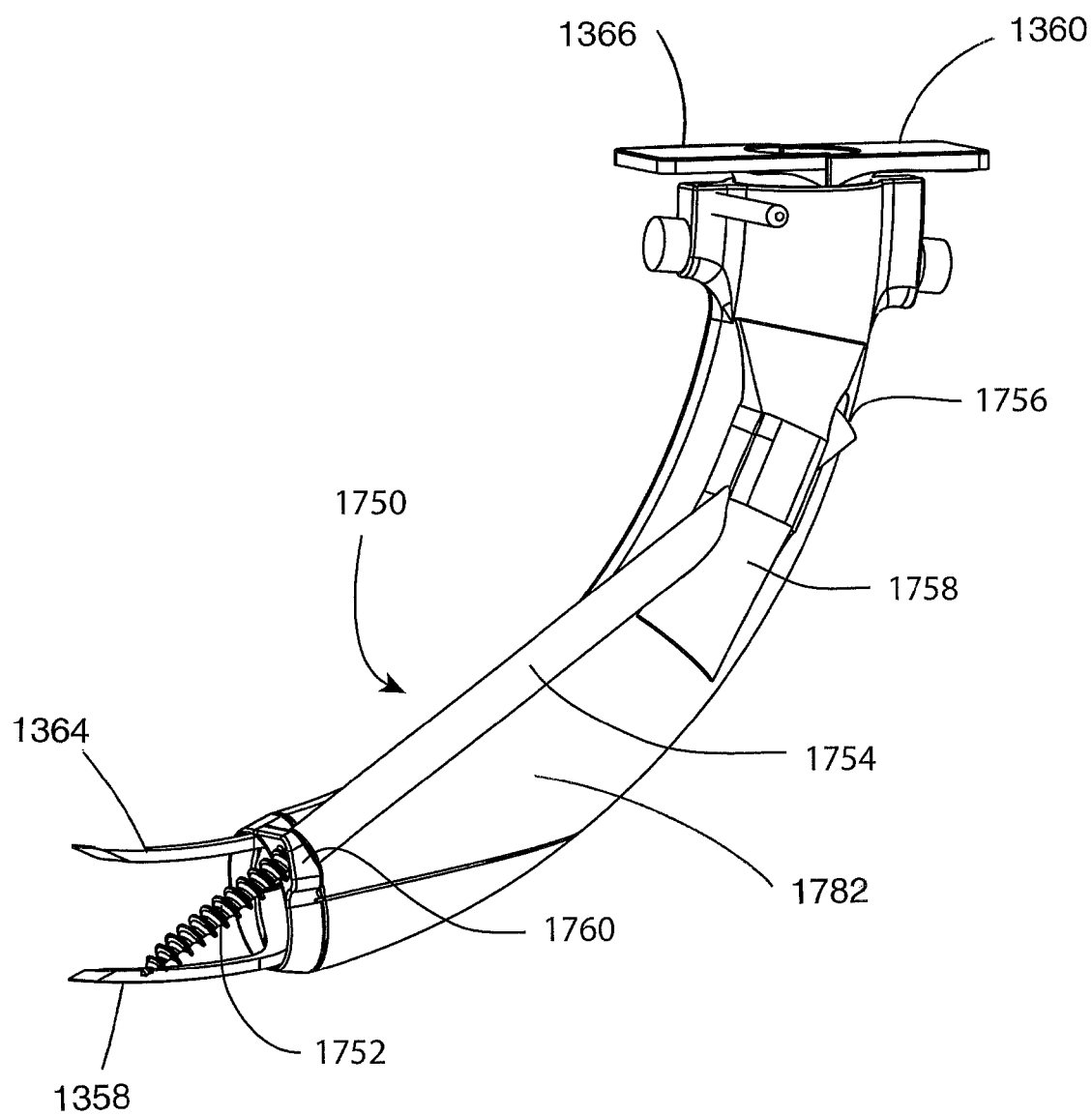
FIG. 36 is a perspective view of the arcuate cannula, tang assembly and vertebral body docking assembly of FIG. 35.

Referring to FIG. 36, a caudal vertebral body docking assembly 1750 includes a bone screw 1752, and a guide sleeve 1754. Guide sleeve 1754 is generally tubular in form and may be monolithically formed with arcuate cannula 1782, or removably coupled to arcuate cannula 1782 through a first guide bracket 1758. Guide sleeve 1754 provides a lumen 1756 though which the bone screw 1752 may be inserted.

A driver (not shown) may be inserted into the lumen 1756 to drive the bone screw 1752 into a vertebral body. A head on the bone screw 1752 engages with a second guide bracket 1760 positioned on the distal end of the cannula 1782, preventing the bone screw 1752 from exiting the lumen 1756, and fastening the cannula 1782 to the vertebral body.

Figure 37:
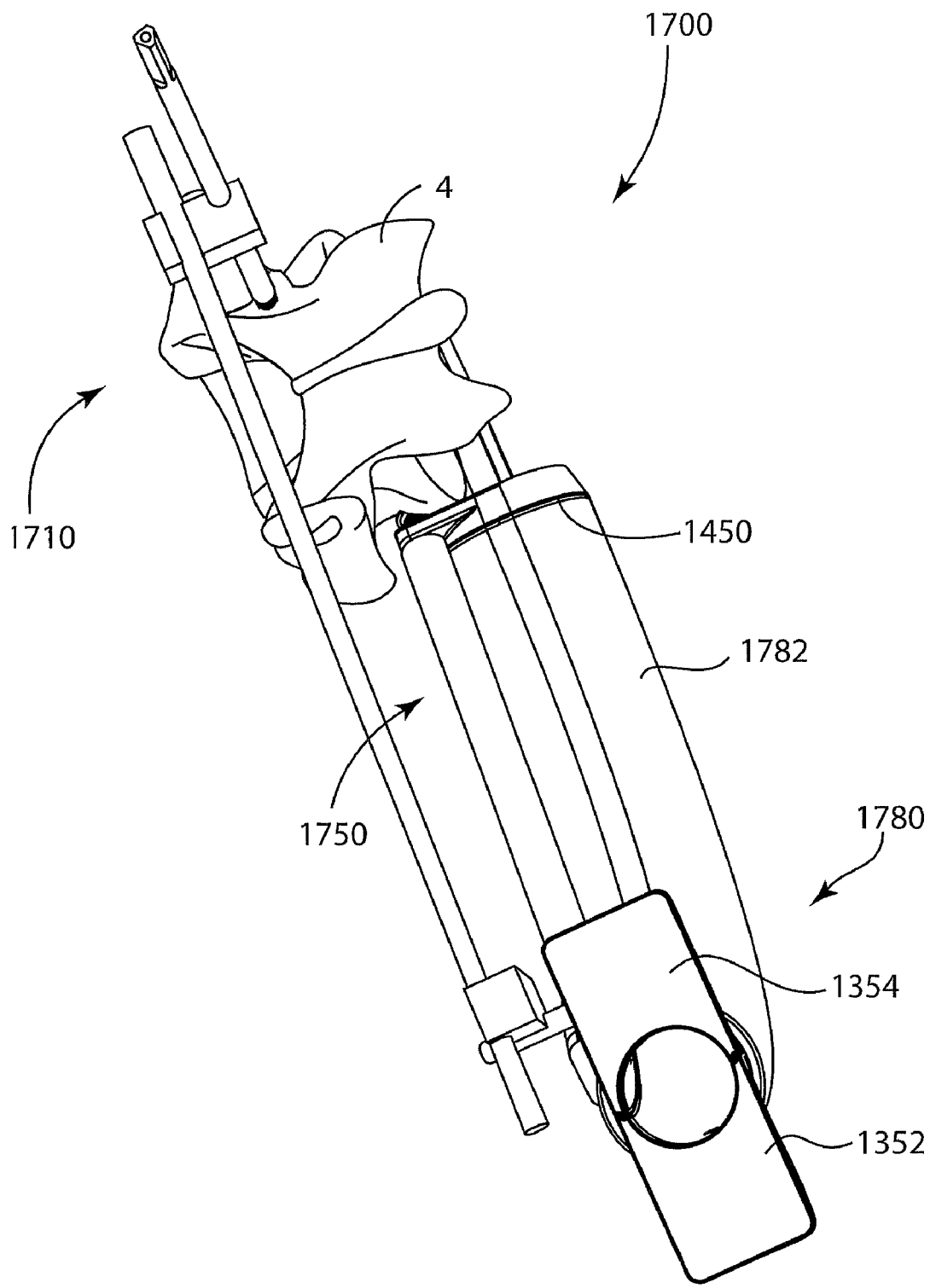
FIG. 37 is a posterior view of the arcuate cannula, tang assembly, pedicle docking assembly and vertebral body docking assembly, and spine of FIG. 35.

Referring to FIG. 37, a posterior view demonstrates how pedicle docking assembly 1710 and vertebral body docking assembly 1750 may be deployed simultaneously to support and stabilize a spinal access cannula assembly 1780. Of course, each system 1710, 1750 may be used independently to support a spinal access cannula assembly. Pedicle docking assembly 1710 secures arcuate cannula 1782 to the right side pedicle on vertebra 4, and vertebral body docking assembly 1750 secures arcuate cannula 1782 to the left side of the vertebral body of vertebra 4. This cross-vertebra support, provided on two separate axes, may prevent unwanted rotation of the cannula assembly around the medial-lateral axis and prevent unwanted translation of the cannula assembly along the medial-lateral access.

As indicated in FIG. 36, it is appreciated that anterior 1352 and posterior 1354 tang portions (FIG. 22 and FIG. 37) may be inserted into arcuate cannula 1782 to provide tissue retraction. The tang portions are partially visible with anterior tang extension 1358, posterior tang extension 1364, posterior handle 1366, and anterior handle 1360. Additionally, arcuate cannula 1782 may include radio-opaque marker system 1450 (FIG. 37), providing a visual referencing system as set forth previously. It is appreciated that any of the spinal access cannula systems disclosed herein may include at least one of the docking assemblies 1710, 1750.

Figure 38:
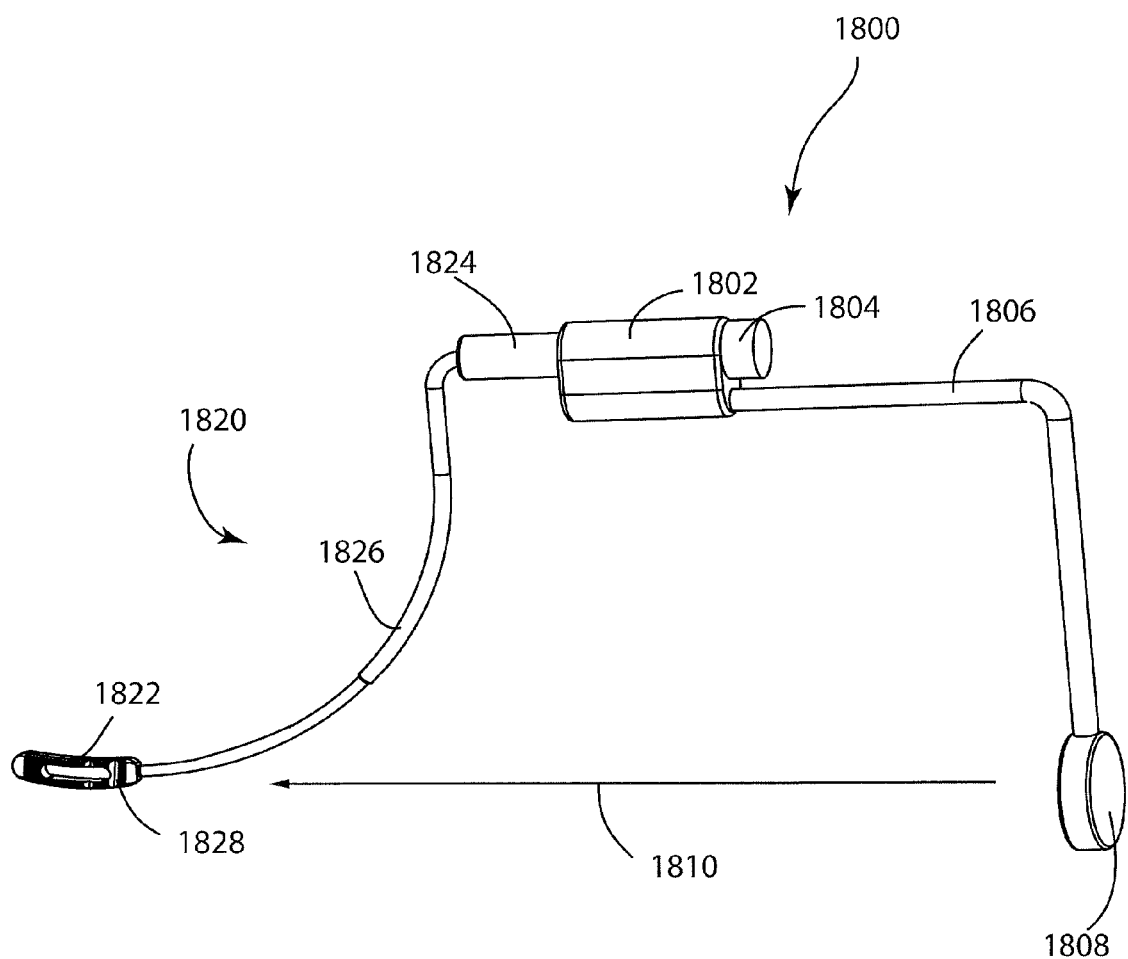
FIG. 38 is a perspective view of a gooseneck tool assembly shaped to be operable through an arcuate cannula.

Referring to FIG. 38, a perspective view of a gooseneck assembly 1800 configured to be operable through an arcuate spinal access cannula is shown, with a tool 1820 comprising a rasp head 1822 secured thereto. Gooseneck assembly 1800 includes a base 1802, a securing member 1804, a neck 1806, and a strike plate 1808. A variety of tools shaped to be inserted through an arcuate spinal access cannula such as cannula 1400 (FIG. 33) may be secured to the assembly 1800, including but not limited to: a rasp, an intervertebral implant trial, an intervertebral implant insertion tool, a curette, discectomy instruments, and annulotomy instruments. Each tool 1820 may comprise a handle 1824 securable to the base 1802, a curved shaft 1826, and a working end or end effector 1828 which in FIG. 38 is a combination of insert trial and rasp head 1822. The means for securing each tool 1820 to the gooseneck assembly 1800 may include a bolt member or other threaded means, a spring pin, a snap fit, a press fit, or a locking pin or nut, among others.

Gooseneck assembly 1800 is configured such that when a force is applied to the strike plate 1808 by a hammer or other means, the component of the force vector perpendicular to the strike plate passes through the end effector 1828 of the attached tool 1820, as indicated by vector 1810.

The present disclosure may be embodied in other specific forms without departing from its spirit or essential characteristics. For example, above are described various alternative examples of systems for accessing intervertebral space. It is appreciated that various features of the above-described examples can be mixed and matched to form a variety of other alternatives. It is also appreciated that this system should not be limited to creating access to the intervertebral space. This arcuate access system may be used to obtain access to any portion of the spine. As such, the described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A curved access cannula with a visual referencing system comprising:
    a curved access cannula wherein at least a portion of the curved access cannula is radiolucent; the curved access cannula having:
    a proximal opening with a proximal center point; and
    a distal opening with a distal center point;
    the distal center point separated from the proximal center point by:
    a distance along a depth axis; and
    an offset on a lateral axis orthogonal to the depth axis;
    a longitudinal plane that bisects the curved cannula along the curved length of the curved cannula and includes the distal center point and the proximal center point;
    a distal plane parallel to the distal opening and perpendicular to the longitudinal plane; and
    a third plane perpendicular to both the longitudinal plane and the distal plane and containing the distal center point;
    a first radio-opaque marker having a U-shaped configuration defined by an intersection of the third plane with a wall of the curved access cannula.

2. The curved access cannula of claim 1, further comprising a radio-opaque marker around a perimeter in a vicinity of the distal opening of the curved access cannula.

3. The curved access cannula of claim 2 wherein the distal opening is a circle.

4. The curved access cannula of claim 1, further comprising a second radio-opaque marker having:
    a first end in a vicinity of the distal opening of the curved access cannula; and
    a second end away from the distal opening of the curved access cannula;
    wherein the first end and the second end are both in the longitudinal plane of the curved cannula.

5. The curved access cannula of claim 4 wherein the first end and the second end are in a curved line that ends in a vicinity of the distal opening at a maximum depth for the curved access cannula.

6. The curved access cannula of claim 1 wherein the distal plane contains a perimeter of the distal opening of the curved access cannula and the radio-opaque marker has a first end and a second end in a vicinity of the distal plane.

7. The curved access cannula of claim 4, wherein the first radio-opaque marker and the second radio-opaque marker are adapted to provide a radio-opaque marker image of a cross hair to provide an indication of position of the distal opening of the curved access cannula relative to another object visible through fluoroscopy.

8. The curved access cannula of claim 7 wherein the radio-opaque marker image of a cross hair is framed by a radio-opaque marker image from a third radio-opaque marker along a perimeter of the curved access cannula near the distal opening.

9. A curved access cannula with a visual referencing system comprising:
    a curved access cannula wherein at least a portion of the curved access cannula is radiolucent; the curved access cannula having:
    a proximal opening; and
    a distal opening;
    a center of the distal opening separated from a center of the proximal opening by:
    a distance along a depth axis; and
    an offset on a lateral axis orthogonal to the depth axis;
    a set of at least one radio-opaque marker in contact with the curved access cannula to allow fluoroscopic visualization of the set of at least one radio-opaque marker to provide an indication of the position of the distal opening relative to another object visible through fluoroscopy; and
    a first radio-opaque insert that extends through the curved access cannula and beyond the distal opening of the curved access cannula; the radio-opaque insert having a radiolucent window to allow the set of at least one marker to be viewed through fluoroscopy.

10. The curved access cannula of claim 9 where the radiolucent window is an opening in the radio-opaque material.

11. The curved access cannula of claim 9 further including a second radio-opaque insert that combines with the first radio-opaque insert to form a curved channel with at least one radiolucent window, the curved cannula fitting within the curved access cannula.

12. The curved access cannula of claim 1 further comprising a guide sleeve attached to the curved access cannula and providing a pathway for a bone screw to be advanced from a proximal sleeve opening near the proximal opening of the curved access cannula to a distal sleeve opening near the distal opening of the curved access cannula so that a bone screw may be used to anchor the distal end of the curved access cannula to a portion of a patient's anatomy.

13. A curved access cannula with a visual referencing system comprising:
   a radiolucent curved cannula with:
      a distal opening and a distal center point;
      a proximal opening with a proximal center point;
      a depth axis;
      a longitudinal plane that bisects the curved cannula along the curved length of the curved cannula and includes the distal center point and the proximal center point;
      a distal plane parallel to the distal opening and perpendicular to the longitudinal plane; and
      a third plane perpendicular to both the longitudinal plane and the distal plane and containing the distal center point;
   a first marker along a perimeter of the curved cannula and in the distal plane, the first marker intersecting the third plane at two points;
   a second marker in the longitudinal plane with a minimum depth that matches a minimum depth for the first marker and a maximum depth that matches a maximum depth for the first marker;
   a third marker in the third plane connecting the two points of intersection of the first marker with the third plane;
   the first, second, and third markers being sufficiently radio-opaque to provide a cross hair radio-opaque marker image in a fluoroscopic image of the curved cannula looking through a portion of the curved cannula towards the distal opening.

14. A curved access cannula with a visual referencing system comprising:
   a curved access cannula that is at least mostly radiolucent with a perimeter along a distal end of the curved access cannula; and
   a set of separate radio-opaque markers each providing a radio-opaque image that, when viewed fluoroscopically through at least a portion of the radiolucent curved access cannula towards the distal opening of the access cannula, combine together to create a radio-opaque cross hair image without the set of markers obstructing the distal opening of the access cannula
   wherein the set of markers includes a radio-opaque marker along a perimeter of the curved access cannula near the distal opening
   wherein the set of markers that provide a radio-opaque image to provide a cross hair image are adapted to have one marker substantially in an anterior/posterior direction and one marker in substantially a caudal/cephalad direction when the curved access cannula system is used with an intended approach that places a depth axis of the curved access cannula at an oblique angle with respect to the anterior/posterior orientation of a targeted intervertebral disc space.

* * * * *